(12) United States Patent
Dysarz

(10) Patent No.: US 6,228,054 B1
(45) Date of Patent: May 8, 2001

(54) INTERCHANGEABLE SAFETY NEEDLE CANNULA MODULE THAT IS ACTIVATED BY A SAFETY SYRINGE AND PLUNGER MODULE

(75) Inventor: Edward D. Dysarz, 18 Front St., Rockport, TX (US) 78382

(73) Assignee: Edward D. Dysarz, Rockport, TX (US)

( * ) Notice: Subject to any disclaimer, the term of this patent is extended or adjusted under 35 U.S.C. 154(b) by 0 days.

(21) Appl. No.: 09/591,951

(22) Filed: Jun. 12, 2000

Related U.S. Application Data

(63) Continuation-in-part of application No. 09/453,393, filed on Dec. 3, 1999, now Pat. No. 6,099,500.

(51) Int. Cl.[7] .................................................. A61M 5/00
(52) U.S. Cl. ........................................... 604/110; 604/195
(58) Field of Search .................................... 604/110, 187, 604/195, 218, 263

(56) References Cited

U.S. PATENT DOCUMENTS

| | | |
|---|---|---|
| 4,973,316 | 11/1990 | Dysarz . |
| 4,978,343 | 12/1990 | Dysarz . |
| 5,019,044 | 5/1991 | Tsao . |
| 5,084,018 | 1/1992 | Tsao . |
| 5,201,710 | 4/1993 | Caselli . |
| 5,267,961 | 12/1993 | Shaw . |
| 5,407,436 | 4/1995 | Toft et al. . |
| 5,769,822 | 6/1998 | McGary et al. . |
| 6,010,486 | 1/2000 | Carter et al. . |
| 6,050,974 | 4/2000 | Allard . |
| 6,066,115 | 6/2000 | Chang Lai . |

FOREIGN PATENT DOCUMENTS

| | | |
|---|---|---|
| 6033386 | 2/2000 | (CA) . |
| 6056724 | 4/2000 | (FR) . |

*Primary Examiner*—John D. Yasko
(74) *Attorney, Agent, or Firm*—Streets & Steele; Jeffrey L. Streets

(57) ABSTRACT

A safety needle cannula module that is interchangeable in combination with a safety syringe and plunger module, wherein the safety needle cannula module is formed with one of a variety of needle cannula sizes and wherein a safety syringe may be one of a variety of syringe sizes. The safety needle cannula module with needle cannula of desired size is attached to a safety syringe module wherein said safety syringe module is a desired size. After medication is injected into a body with the safety needle cannula and the safety syringe, the safety syringe module reacts with the safety needle cannula module and further causes said safety needle cannula to automatically retract and be disposed within the hollow plunger within said safety syringe module.

20 Claims, 34 Drawing Sheets

FIG. 11
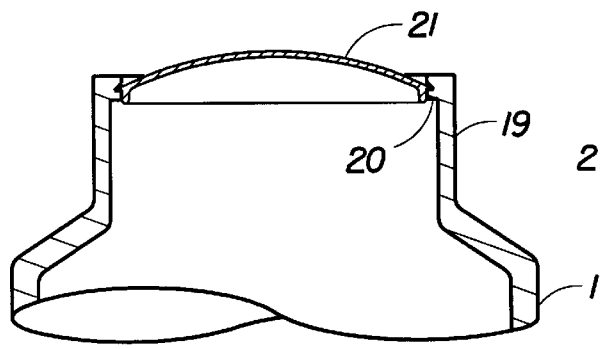
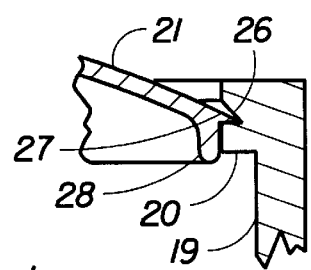
FIG. 12A
FIG. 12
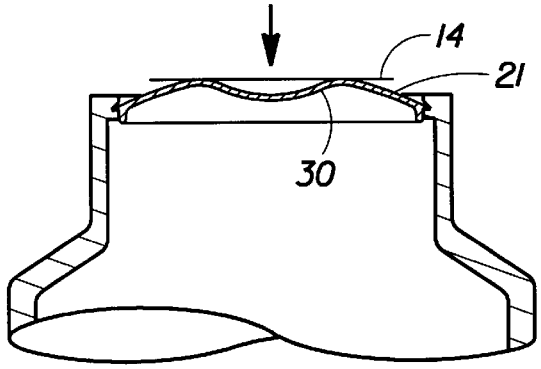
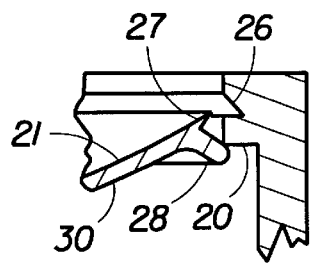
FIG. 12B
FIG. 13
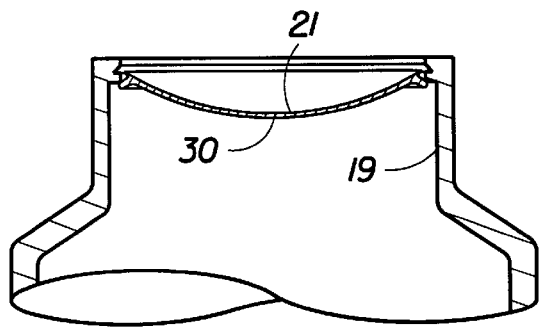
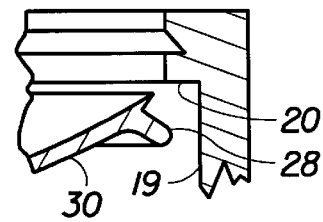
FIG. 12C
FIG. 14
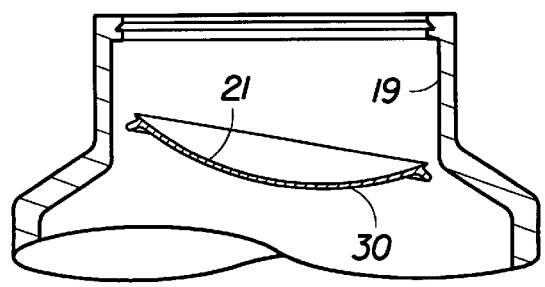

INTERCHANGEABLE SAFETY NEEDLE CANNULA MODULE THAT IS ACTIVATED BY A SAFETY SYRINGE AND PLUNGER MODULE

This application is a continuation-in-part of U.S. patent application Ser. No. 09/453,393 filed on Dec. 3, 1999 now U.S. Pat. No. 6,099,500.

BACKGROUND OF THE INVENTION

1. Field of the Invention

This invention relates to a single use syringe for injecting medicine into a patient. More particularly, the invention relates to a safety syringe having a retractable needle cannula that renders the needle cannula harmless after it is used.

2. Background of the Related Art

Many communicable diseases can be spread through the penetration or scratching of the skin by a needle that was previously used by another having a disease. Spreading of the disease in this manner may occur by accident, such as with medical personnel making injections, or it may occur through misuse, such as by intravenous drug users using a previously used needle cannula.

Various syringes have been invented, designed and developed to retract the needle into the syringe or the plunger inside of the syringe. Some of these devices are U.S. Pat. No. 4,973,316 (Dysarz), U.S. Pat. No. 4,978,343 (Dysarz), U.S. Pat. No. 5,180,369 (Dysarz), U.S. Pat. No. 5,267,961 (Shaw), U.S. Pat. No. 5,019,044 (Tsao), U.S. Pat. No. 5,084,018 (Tsao), U.S. Pat. No. 5,385,551 (Shaw), U.S. Pat. No. 5,389,076 (Shaw), U.S. Pat. No. 5,201,710 (Caselli), U.S. Pat. No. 5,407,436 (Toft et al), U.S. Pat. No. 5,769,822 (McGary et al), and U.S. Pat. No. 6,010,486 (Carter et al). These designs have needles which retract at the end of the injection. Most of these designs have not reached the market due, at least in part, to problems associated with expense of manufacturing, poor reliability or user acceptability. However, even though some of these designs operate poorly are costly, they have still been commercialised due to the great need in hospitals or clinics for any type of safety syringe.

Most of the existing safety syringe designs allow for automatic retraction of the needle cannula into the plunger barrel of the syringe when the plunger is fully extended into the syringe. The automatic retraction is triggered when the plunger makes physical contact with the distal end of the syringe barrel. Typically, the end of the plunger is provided with a disengageable or sacrificial member at the distal end and the needle cannula is secured by a disengageable or sacrificial member. When the plunger reaches the fully extended position, the physical contact between the plunger and the needle cannula causes activation of the two respective disengageable or sacrificial members. In this manner, the end of the plunger barrel is opened and presented to receive the needle cannula. The needle cannula, no longer secured in position, is biased into the plunger barrel by a spring.

Conventional syringes are typically available in modular systems or kits in which approximately ten different sizes of syringes and approximately ten different sizes of needle cannulas can be used interchangeably. This allows an inventory of twenty items to be used in approximately 100 different combinations in accordance with the present need. However, the safety syringes presently available and described in the above patents are not modular and require stocking of an integral safety syringes for each combination of syringe size and needle cannula size desired, for example 100 different safety syringes. Particularly, in light of the greater cost these syringes, the cost, distribution and storage of safety syringes is much greater than conventional syringes.

Despite the prevalence of modular convention syringes, the emergence of a multitude of safety syringe designs and the increasing public outcry for safety syringes, the complexities of the safety syringe mechanisms have limited the number of attempts to design a safety syringe that is modular. Two such attempts include modular syringe tip designs that are combined with a conventional syringe as described in U.S. Pat. No. 5,891,093 (Dysarz) and U.S. Pat. No. 5,935,113 (Dysarz). Compared with the foregoing automatically retracting safety syringes, these two designs can be considered to have safety needle cannula assemblies that are self-contained and manually operated, while being connectable to a conventional syringe and with a conventional locking arrangement. While these devices serve the aforementioned need for modularity, the obvious drawbacks to the devices include the manual retraction mechanism and the additional length that the needle cannula assembly adds to the syringe.

Another deign utilises a modified luer-lok that requires pressed fittings, a cutting ring and a fiangible position that are to be activated or actuated at the same time requiring more strength in the hands and fingers of the user which many medical people do not have. Still another problem with this design is that the needle cannula must be pushed and moved in the direction of the distal end of the needle cannula and if the needle cannula is in an artery or a vein at the time, the needle cannula will pierce the other side of the artery or vein and deposit medication into an undesirable area of the body. Still yet another problem with this design is that the plunger tip must enter a restricted area of the luer-lok and restrict and trap the medication still contained in the area of the stopper. And still yet another problem with this design is that when the outer hub is being attached to the luer-lok, the proximal end of the inner hub could be hit by the distal end of the luer-lok fitting and cause the frangible portion to break or otherwise fail.

Therefore, there remains a need for a modular safety syringe system or kit that provides a selection of syringe modules having various sizes and a selection of needle cannula modules having various sizes that can be combined on site to form an automatically retractable safety syringe of a desired configuration. It would be desirable if the automatically retractable safety syringe has similar length and usability as a conventional syringe. It would be further desirable if the used automatically retractable safety syringe was compact and secure against accidental needle sticks.

SUMMARY OF THE INVENTION

The invention provides a kit of components for assembling modular safety syringes. The kit comprises two or more safety syringe modules having different diameters and two or more safety needle cannula modules. Each safety syringe module has a syringe barrel; a safety plunger extending through a proximal end of the syringe barrel, wherein the safety plunger having a plunger barrel, a sliding gasket formed along the perimeter of the plunger barrel near the distal end for the sealing plunger against the interior sidewalls of the syringe barrel, and a rigid member adjacent the sealing member; and a connector formed in the distal end of the syringe barrel. Each of the two or more safety needle cannula modules have a housing having a connector formed at a proximal end of the housing and a cannula passage formed through a distal end of the housing; a needle cannula extending through the cannula passage; a slidable piston flange coupled to the needle cannula; a retaining member securing the slidable piston flange in the proximal end of the housing; and a spring disposed within the housing to bias the slidable piston flange in the direction of the plunger opening from the distal end towards the proximal end. The connectors in the two or more safety syringe modules are sealably securable to the connectors in the two or more safety needle cannula modules. Accordingly, securing any one of the two or more safety syringe modules provides alignment of the rigid member of the plunger with the retraining member of the safety needle cannula module and alignment of the slidable piston flange with the sealing member of the plunger.

Preferably, the rigid member of the plunger is an end ridge, probably slopped. The retaining element is selected from a shear plate, break plate, a friction ring, a sacrificial membrane, or a snap on ring. Where the retaining element is a shear plate or a break plate, it may optionally include first and second concentric notches formed therein, preferably such that the rigid member is aligned to contact the retaining element between the first and second concentric notches. Similarly, the sealing member is selected form a break plate, a friction plug, a sacrificial membrane, a snap on plug. The connectors are selected from threads, luer-loks, or snap-on fittings.

Another aspect of the invention provides an improvement to a medical device having an elongated hollow body; a moveable hollow member slidable axially in the body; a retraction mechanism including a needle extending from the body for injecting of collection fluid, a needle holding member having an unretractable position, a spring for applying retraction force to the needle holding member in a retraction direction, and a retaining element capable of holding the needle holding member against the retraction force provided by the spring; and a cap releasably sealing a passage in the end of the moveable hollow member that is positioned within the body; the retaining element being triggered to retaining the needle holding member for retraction of the needle in response to selective movement of the moveable member, and the cap being retained from the passage of the movable hollow member in response to the selective movement of the hollow member. The movement omprises a sloping end ridge formed on the end of the moveable hollow member to contact the retaining element upon selective movement of the moveable member. For example the retaining element may be selected from a break plate, a friction ring, a sacrificial membrane, or an interference fit and may be triggered by failing, sliding, or disengaging. Particularly, the retaining element or cap may be sloped along the sloping end ridge.

Yet another aspect of the invention provides an improvement to a medical device having an elongated hollow body; a movable hollow member slidable axially in the body; a retraction mechanism including a needle extending from the body for injecting or collecting fluid, a needle holding member having an unretracted position, a spring for applying retraction force to the needle holding member having an unretracted position, a spring for applying retraction force to the needle holding member in a retraction holding member in a retraction direction, and a retaining element capable of holding the needle holding member against the retraction force provided by the spring; and a cap releasably sealing a passage in the end of the moveable hollow member that is positioned within the body; the retaining element being triggered to release the needle holding member for retraction of the needle in response to selective movement of the moveable member, and the cap being released from the passage of the moveable hollow member in response to the selective movement of the moveable member. The improvement comprises a spring shield coupled to the needle holding 10 member and extending around the spring, wherein the spring is disposed concentrically around the needle, where the spring shield has a outer diameter that is less than that of an internal diameter of the passage of the moveable hollow member.

BRIEF DESCRIPTION OF THE DRAWINGS

So that the above recited features and advantages of the present invention can be understood in detail, a more particular description of the invention, briefly summarised above, may be had by reference to the embodiments thereof which are illustrated in the appended drawings. It is to be noted, however, that the appended drawings illustrate only typical embodiments of this invention and are therefore not to be considered limiting of its scope, for the invention and are therefore not to be considered limiting of its scope, for the invention may admit to other equally effective embodiments.

FIG. 11 is an enlarged section elevation of the pop out dome in the plunger module.

FIG. 12 is an enlarged section elevation of the pop out dome as it would be compressed or pushed in.

FIG. 12A is a section elevation of the outer periphery of the pop out dome.

FIG. 12B is a section elevation of the pop out dome rotating.

FIG. 12C is a section elevation of the pop out dome being popped out.

FIG. 13 is a section elevation of the pop out dome in an inverted position.

FIG. 14 is a section elevation of the pop out dome falling into the plunger module.

FIG. 40 is a section elevation of the tab ring as taken through

FIG. 39.

DETAILED DESCRIPTION OF THE PREFERRED EMBODIMENT

Figure 1:
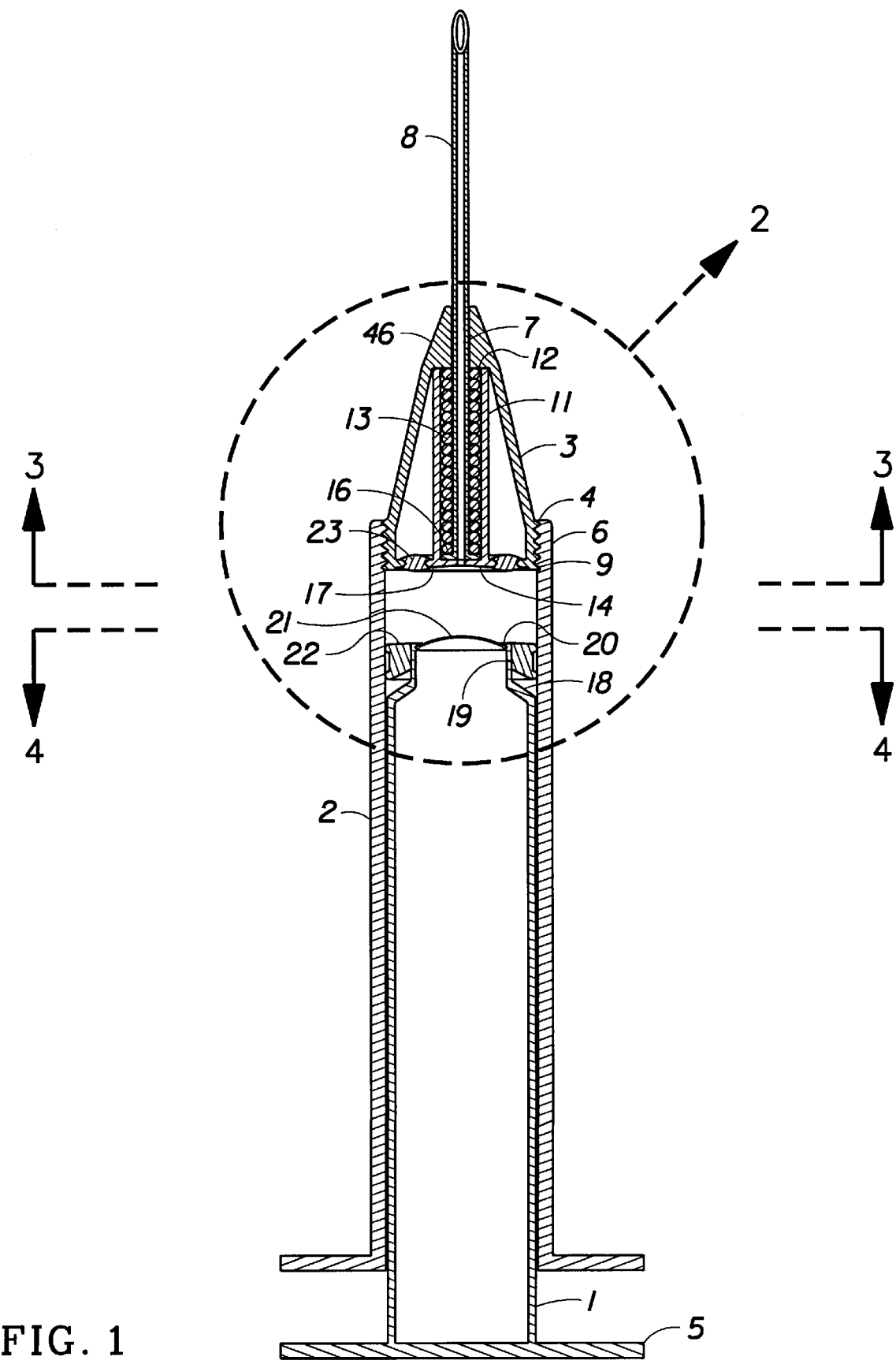
FIG. 1 is a section elevation view of the safety needle cannula module fixed to the distal end of the safety syringe and plunger module.

The present invention provides a modular safety syringe system or kit that provides a selection of safety syringe modules having various sizes and a selection of needle cannula 8 modules having various sizes that can be combined on site to form an automatically retractable safety syringe of a desired configuration. In addition to requiring a common interface between a safety syringe module and a needle cannula module, as with conventional modular systems, the present invention also requires and facilitates a specific co-operation relationship between the syringe plunger module and the needle cannula module.

Each safety syringe module of the present invention includes a single barrel, a safety plunger extending through a proximal end of the syringe barrel, and a connector formed in the distal end of the syringe barrel. A syringe barrel may be of any length and diameter, as dictated by the volume of fluid to be delivered, through the syringe, and will include a connector have a fixed diameter. In systems, sets or kits having a plurality of syringes with different diameters, each syringe should have a connector with a common diameter and a common connection type. For example, three syringe barrels may be provided with diameters 2, 2.5, and 3 centimeters, respectively, but each of the three syringe barrels should have a connector of the same type, such as threads, and of the same diameter, such as 1.5 centimeters. It should be recognised that sets having syringes with wide variations in single barrel diameter, the set may include a first subset of syringes having a first common connector with a first common diameter and a second subset of syringes having a second common connector with a second common diameter. The present invention contemplates any number of subsets, each subset having the same or different type of connector, and each subset having the same or different connector diameter. It should be recognised that the term "diameter" as used herein shall not be limited to the dimensions of a circular opening, but shall include the dimensions of any shape of the opening, for example shapes like squares, triangles, ovals and rectangles.

The safety plungers of the present invention have suitable lengths and diameters to work in a co-operative relationship inside the syringe barrel. It is anticipated that each syringe of a different diameter will have a corresponding safety plunger of suitable size. The safety plunger has a plunger barrel, a sliding gasket formed along the perimeter of the plunger barrel near the distal end for sealing the plunger against the interior side walls of the syringe barrel, and a removable member sealing a central opening in the distal end of the plunger barrel. The safety plunger will also include a lip or smaller structure that engages a critical portion of the needle cannula module as described below.

The safety needle module has a connector that is designed to be coupled to the connector on the safety syringe module. The connectors may be of various types, including but not limited to male/female threads, snap on, and luer-lok tips. In systems, sets or kits having a plurality of safety needle modules with different cannula diameters, gauges, types or lengths, each safety needle module should have a connector with a common diameter and a common connection type. For example, three safety needle modules may be provided with, but not limited to, 16G, 20G, and 30G cannulas, respectively, but each of the three modules should have a connector of the same type, such as male threads, and of the same diameter, such as 1.5 centimeters. Furthermore, it should be recognised that the safety needle modules will preferably all have the same type of connector, such as male threads or the male portion of the luer-lok, and the safety syringe modules will preferably all have the same type of connector that mates the needle module connector, such as female threads of the female portion of the luer-lok. In the case where there are subsets of syringes having connectors with different diameters, then there will also be subsets of safety needle modules having connectors with the same mating diameters.

The safety needle cannula includes a housing having the connector at the proximal end and a cannula passage through the distal end. A needle cannula coupled to a slidable position flange extends through the cannula passage. The slidable position flange is secured to the housing by a disengageable, sacrificial or retaining member. A spring is disposed within the housing to bias the slidable piston flange, and consequently the needle cannula, away from the distal end towards the proximal end. The spring surrounds the needle cannula and is maintained in a biased or spring loaded condition between the distal end of the housing and the slidable piston flange. It is important that the spring provide sufficient force to move the needle cannula into the plunger barrel upon release, but the spring should not be so strong as to fatigue or cause failure to the housing.

It should be recognised that the disengageable or sacrificial members in the safety plunger and the safety needle module may take many forms, including plates that can fail, break or shatter as described in U.S. Pat. No. 5,180,369 (Dysarz) incorporated by reference herein, frictionally engaged retaining rings and plugs as described in U.S. Pat. No. 5,285,551 incorporated by reference herein, sacrificial membranes, interference fits, and the like.

It is a critical aspect of the invention that a rigid component of the safety plunger is disposed at an appropriate position to engage and actuate the retaining member in the safety needle module and that a rigid component of the safety needle module is disposed at an appropriate position to engage and actuate the sealing member in the safety plunger. Since syringes typically have cylindrical barrels, although they could just as well have any shaped cross-section, the positions of the two rigid components, the sealing member and the retaining member can be described in terms of concentric members having a specific radial distance from the axial centerline of the needle cannula. While tow of the concentric members are in the safety plunger and the two other concentric members are in the needle module, the members must achieve a standard, fixed or consistent co-operative relationship when assembled and, consequently, must have standard radii or other dimension and threads specified for each of the two rigid components, the sealing member and the retaining member. For any given set or subset of safety syringe modules and safety needle modules, the radii musts be the same regardless of the syringe diameter or the cannula gauge. In other words, the size and alignment of the members accounting for the automatic retraction must be consistent in order for the retraction to occur.

Consistent alignment of the members, including alignment of a rigid plunger member with the needle retaining member and alignment of the rigid safety needle member with the plunger sealing member, can be achieved either by (a) using a constant plunger barrel diameter regardless of syringe diameter, or (b) using plunger barrels having a diameter just smaller than the syringe barrel, but having a diameter at the distal end that is reduced, or perhaps even increased, to form or achieve the fixed radii of the rigid plunger component. The former option is less desirable, because the plunger barrel could wobble from side to side and the gasket member would not receive as much physical support.

Now referring to the Figures, FIG. 1 is a section elevation view of the system or kit of the first preferred embodiment of the present invention. The system includes a separate safety syringe module and a safety needle cannula module 3. The safety syringe module includes a safety plunger 1 and a syringe module 2. A syringe connector 6 is shown formed in the distal end of the syringe module 2, preferably forming a set of female threads. The syringe module 2 is a hollow elongated barrel with an inside surface and an outside surface. The safety plunger is shown disposed within the syringe barrel 2 with a thumb flat 5 shown at the proximal end of the safety plunger.

The safety needle cannula module 3 is shown as hollow with an inside surface and an outside surface and with a needle cannula 8 extending form the distal end of a housing 46 having male threads 9 that are attachable to the female threads 4 formed on the syringe connector 6 of the syringe module 2. The needle cannula 8 is shown extending from the support tunnel 7 shown formed in the distal end of the safety needle cannula module 3. The spring shield 11 is shown near the cannula flat 12. The distal end of the biased spring 13 is shown thrusting on the cannula flat 12 and the proximal end of the biased spring is shown thrusting on the needle base plate 14. The needle base plate 16 is shown disposed on and thrusting on the base plate 14 that is on the proximal end of the spring shield 11. The base plate flange 17 is shown extending from the base plate. The retaining ring 23 is shown forming a liquid tight seal while retaining the needle cannula in the safety needle cannula module.

The distal end of the plunger module is shown with a reduction cone 18 and a dome support means 19. The dome support means is suitably fixed to the reduction cone at the proximal end of the dome support means and a dome foundation 20 is formed on the inside of the distal end of the dome support means. A pop out dome 21 is shown suitably disposed in the dome foundation that will be seen more clearly in FIG. 2. A sliding plunger gasket 22 is shown formed on the outside surface of the dome support means.

Figure 2A:
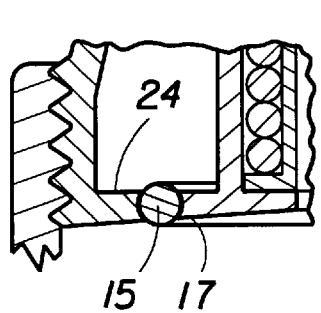
FIG. 2A is an enlarged section elevation showing an 0 ring seal.
Figure 2:
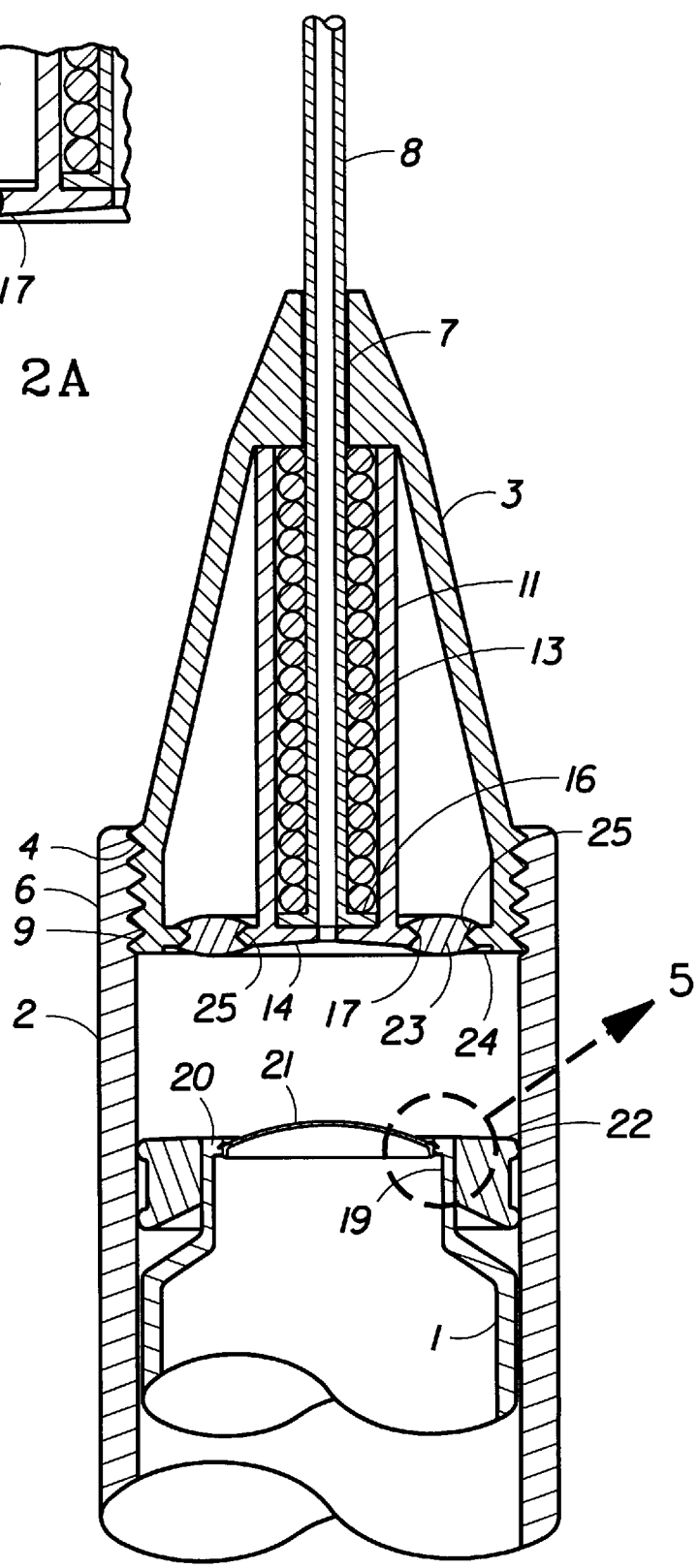
FIG. 2 is an enlarged section elevation of the safety needle cannula module shown fixed to the safety syringe module.

FIG. 2 is an enlarged section elevation of the distal end of the syringe module 2 and the safety needle cannula module 3.

The needle cannula 8 is shown disposed in the support tunnel 7 wherein the needle cannula will be suitably supported when thrust into a body and thereby will not deflect. The needle cannula further extends into and is disposed in the biased spring 13 wherein it could be supported laterally by the biased spring and therefor reduce or eliminate any deflection in the area of the biased spring. The biased spring is further supported and protected by the spring shield 11. The spring shield protects the biased spring 13 as it thrusts the needle cannula into the plunger 1.

The retaining ring 23 is shown forming a fluid tight and gas tight barrier from the modular flange 24 to the base plate flange 17. The retaining ring also retains the, the spring shield 11 and the biased spring 13 and prevents the biased spring from thrusting the needle cannula 8 into the syringe module 2. The retaining ring is shown with V notches 25 formed in the inner periphery and the outer periphery of the retaining ring. The configuration of the V notches matches the bevelled configuration of the outside periphery of the base plate flange 17 and beveled configuration of the inner periphery of the modular flange 24 therein forming a gas tight and fluid tight connection. The retaining ring may be made of rubber, plastic, vinyl or any other soft material and the retaining ring may also be made out of hard material such as glass, plastic, or metal by design choice. The retaining ring in this description is designed to deflect to release the biased spring and the needle cannula, however the module flange and the base plate flange could also be made to fail to release the biased spring and needle cannula. There are a number of configurations that the retaining ring may have such as that shown in FIG. 2A and it should be known that the possible number of configurations is great. All parts of FIGS. 1 through 14 have a distal end and a proximal end.

The pop out dome 21 is shown held in place by the dome foundation 20. The dome foundation 20 is shown more clearly in FIG. 5. The dome foundation is formed on the distal end of the dome support means 19. The proximal end of the dome support means is shown suitably fixed to the distal end of the plunger 1. The dome foundation is formed on the inside surface of the dome support means and the sliding plunger gasket 22 is shown on the outside surface of the dome support means.

Referring to FIG. 2A there is shown a retaining ring 15 that is in the configuration of an O ring in section and acts in the same manner as the retaining ring. The base plate flange and the module flange 24 have rounded configurations to accommodate the O retaining ring.

Figure 3:
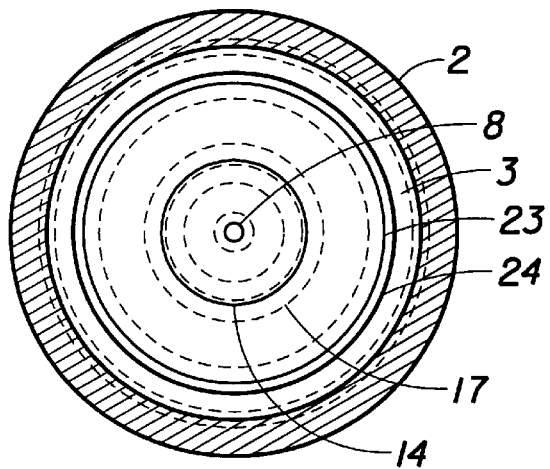
FIG. 3 is a section plan view of the needle cannula module as taken through FIG. 1.

Referring to FIG. 3 there is shown a section plan view of the safety needle cannula module 3 and part of the syringe module 2 as taken through FIG. 1.

The retaining ring 23 is shown held in place by the module flange 24 on the outer periphery and the base plate flange 17 on the inner periphery. The needle cannula 8 is shown in the center of the safety needle cannula module 3 and the base plate 14 is shown near needle cannula 8.

Figure 4:
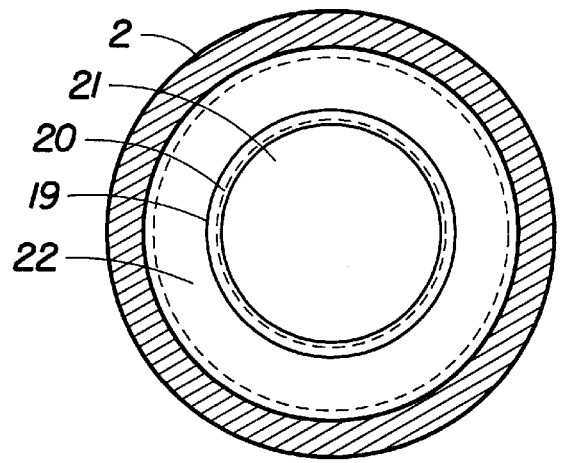
FIG. 4 is a section plan view of the pop out dome in the distal end of the plunger module as taken through FIG. 1.

Referring to FIG. 4 there is shown a section plan view of the pop out dome 21 as taken through FIG. 1.

The pop out dome is shown supported on the dome foundation 20 that is at the distal end of the dome support means 19. The sliding plunger gasket 22 is shown between the dome support means and the syringe module 2.

Figure 5:
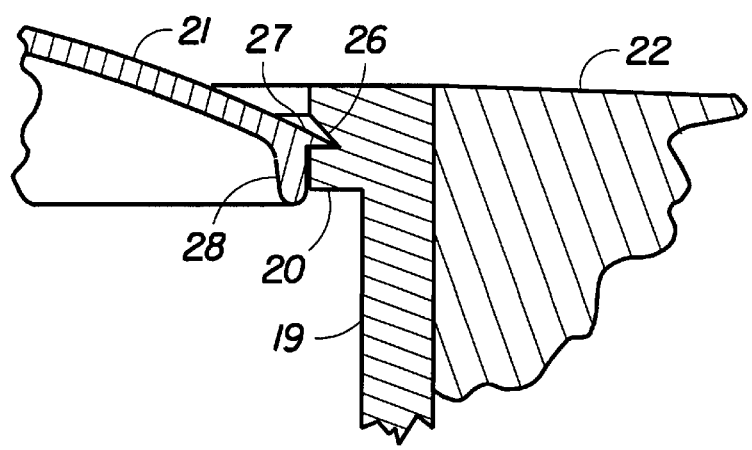
FIG. 5 is an enlarged section elevation of the distal end of the plunger module.

Referring to FIG. 5 there is shown an enlarged section elevation of the dome foundation 20 as then through FIG. 2.

The sliding plunger gasket 22 is shown on the outer periphery of the dome support means 19. The inside surface of the dome foundation 20 is shown of a lesser diameter than the inside surface of the dome support means 19 to allow the pop out dome 21 to fall out of the dome support means unhindered. A dome notch 26 is shown formed in the dome foundation and the dome notch is circumambient in the dome foundation. The dome flange 27 is shown extending the outer periphery 10 of the pop out dome 21 and is disposed in the dome notch 26 forming a fluid tight seal between the dome notch and the dome flange. The fluid tight seal and the gas tight seal could also be formed with adhesive or a gasket between the dome notch and dome flange. The dome trunnion 28 is shown also formed near the outer periphery of the pop out dome and extends from the distal end of the pop out dome to the proximal end of said pop out dome and will be sown in FIGS. 12A, 12B, and 12C as to how the dome trunnion will cause the pop out dome 21 to pop out of the dome foundation.

Figure 6:
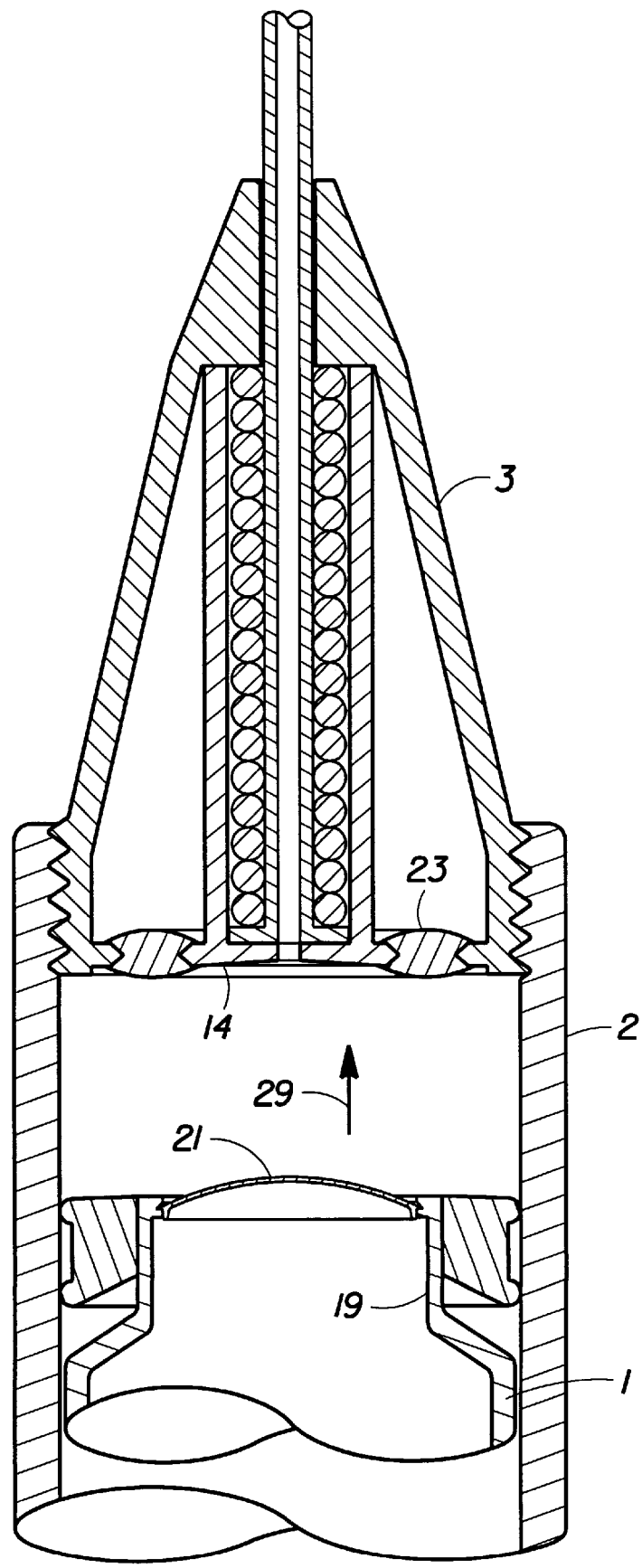
FIG. 6 is an enlarged section elevation of the plunger module moving toward the safety needle cannula module.

Referring to FIG. 6 there is shown an enlarged section elevation of the safety needle cannula module 3 the syringe module 2 and the plunger 1.

The plunger is moving in a cannula direction 29 to force the pop dome 21 into the base plate 14 and to cause the distal end of the dome support means 19 into the retaining ring 23.

Figure 7:
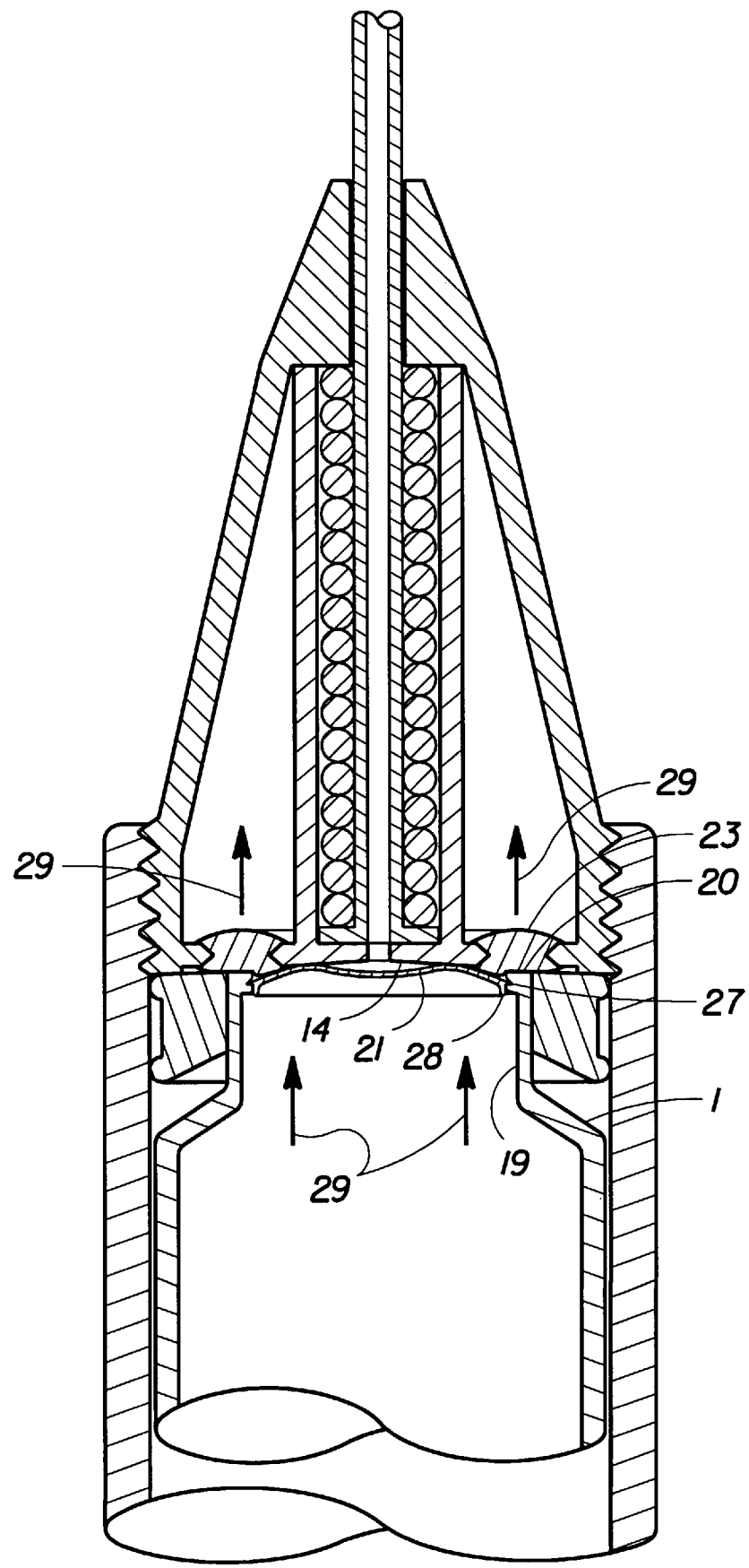
FIG. 7 is an enlarged section elevation of the safety needle cannula module compressing the pop out dome.

Referring to FIG. 7 there is shown an enlarged section elevation of the plunger 1 being thrust in a cannula direction 29.

The distal end of the dome support means 19 and the dome foundation 20 have made contact with the retaining ring 23 and are thereby thrusting on the retaining ring. The base plate 14 is also applying essentially a concentrated load on the pop out dome plate 21 causing the pop out dome 21 to deflect and further starting the dome flange 27 to rotate about the dome trunnion 28.

Figure 8:
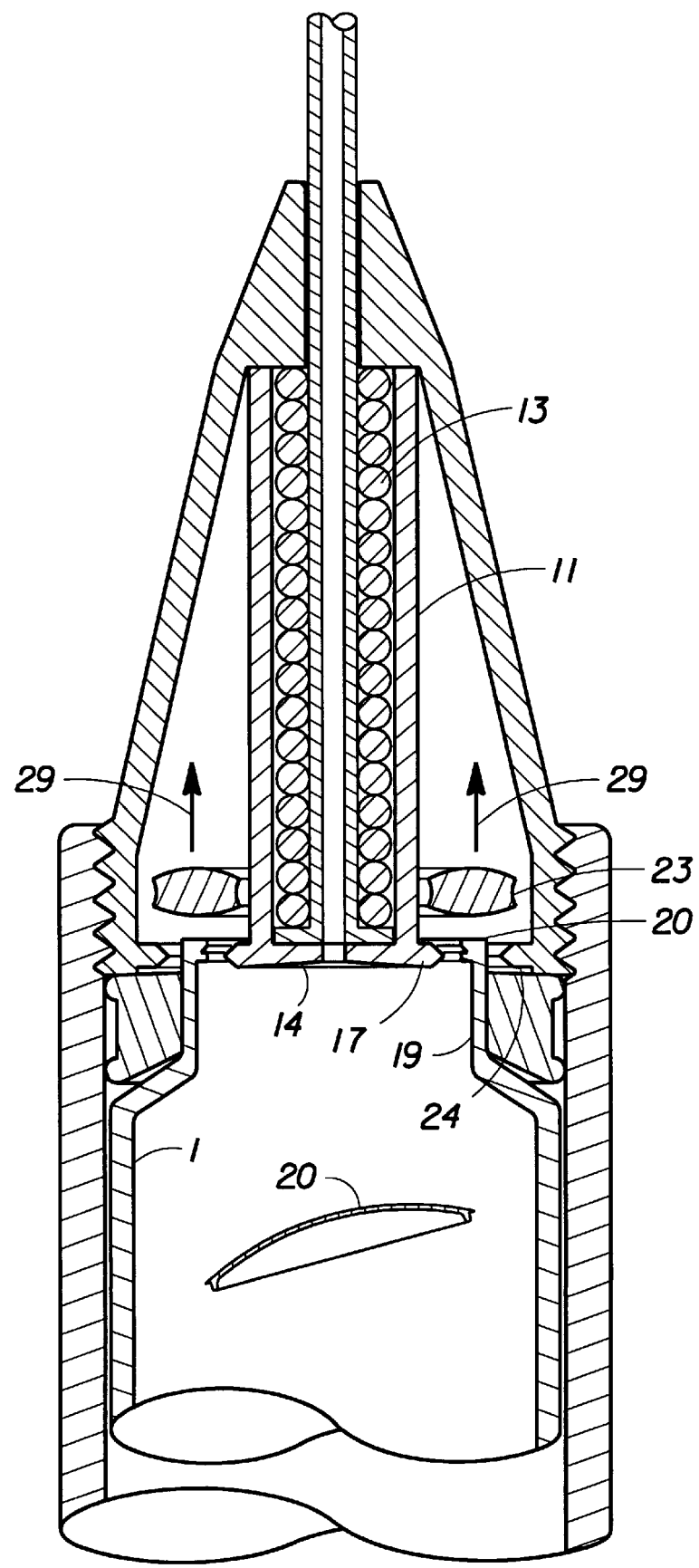
FIG. 8 is a section elevation of the safety needle cannula module popping out the pop out dome.

Referring to FIG. 8 there is shown an enlarged section elevation of the dome support means 19 and the dome foundation having thrust the retaining ring 23 off the base plate flange 17 and the module flange 24 thus freeing the retaining ring, the base plate 14, the spring shield 11 thereby allowing the biased spring 13 to thrust the needle cannula 8 into the plunger 1. The pop out dome 21 has already been popped out of the dome foundation 20 into the inside of the plunger 1.

Figure 9:
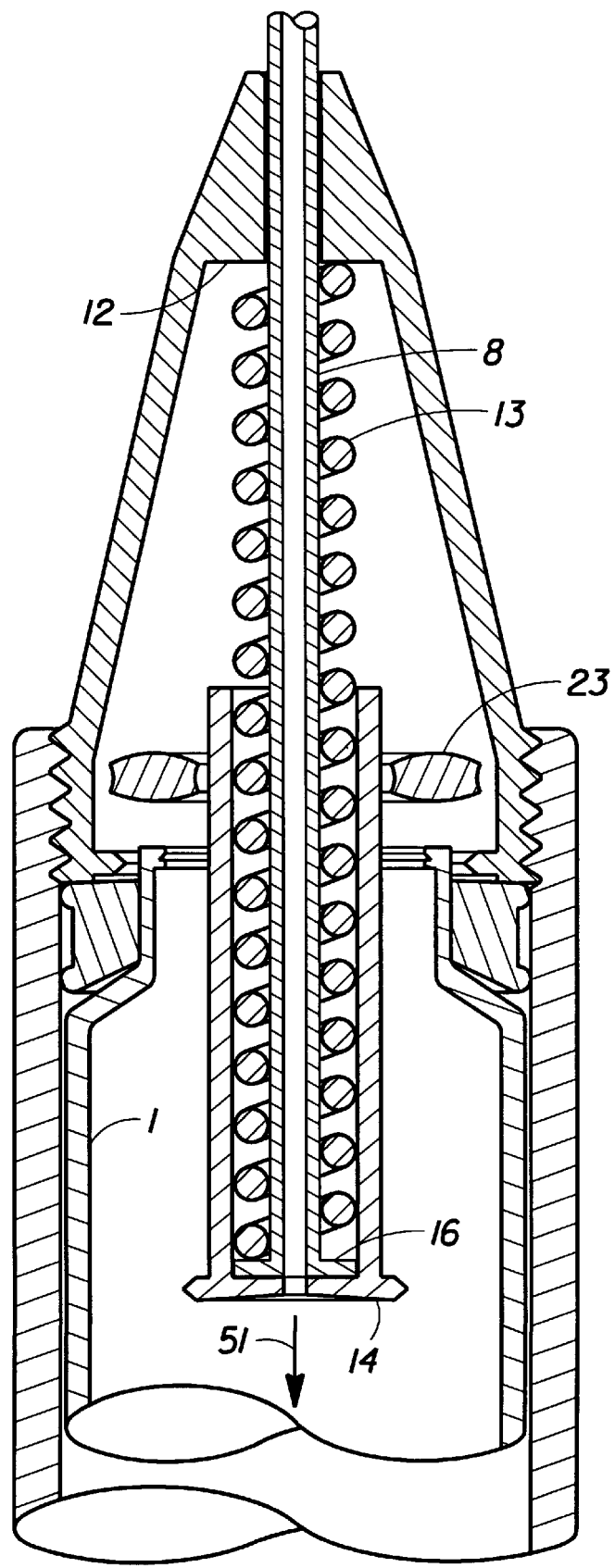
FIG. 9 is a section elevation of the safety needle cannula module thrusting into the plunger module.

Referring to FIG. 9 there is an enlarged section elevation of the needle cannula 8 being thrust into the inside of the plunger 1, The retaining ring 23 is no longer retaining the base plate 14 and spring shield 11 thus allowing the distal end of the biased spring 13 to thrust on the cannula flat 12 and the proximal end of the biased spring to thrust on the needle base plate 16 thus thrusting the needle cannula 8 in a plunger direction 51 into the plunger 1.

Figure 10:
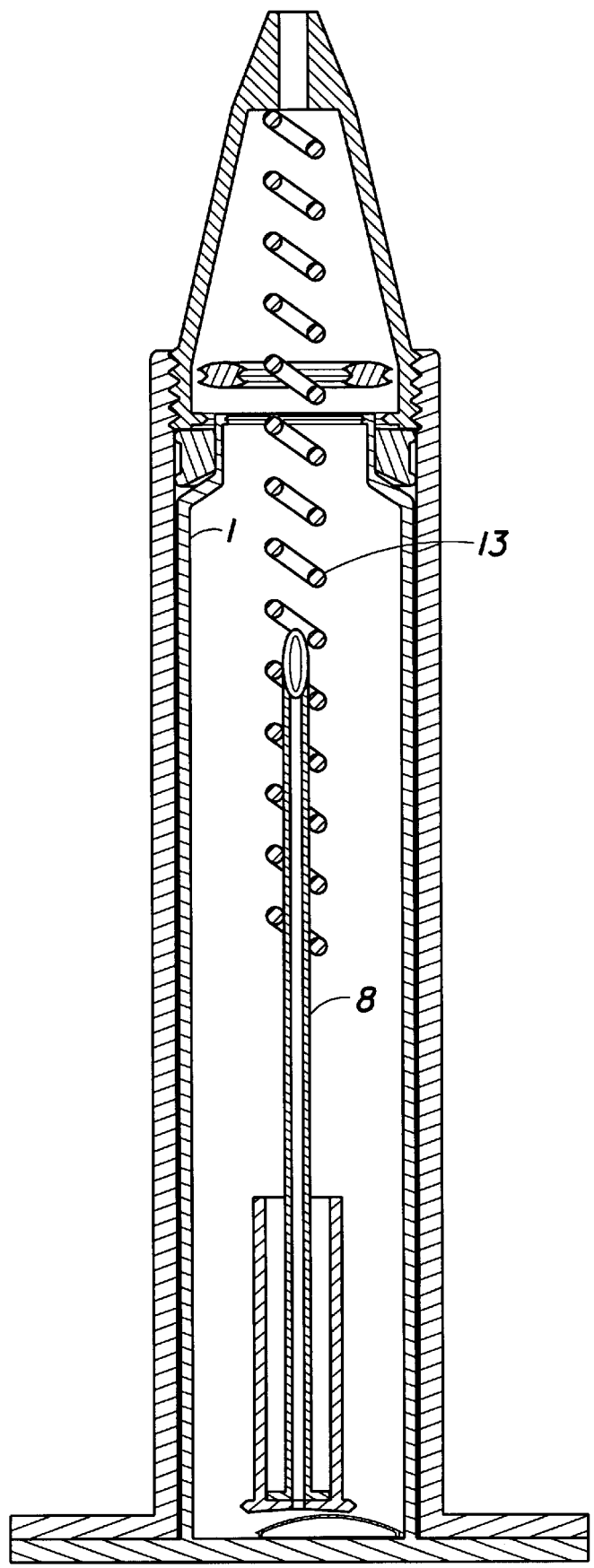
FIG. 10 is a section elevation of the safety needle cannula inside of the plunger module.

Referring to FIG. 10 there is shown a section elevation view of the needle cannula 8 inside of the plunger 1.

The needle cannula 8 cannot fall out of the plunger because it is entangled in the spring 13.

Referring to FIG. 11 there is shown a section elevation of the pop out dome 21 suitably supported in the dome foundation 20 at the distal end of the dome support means 19.

As the plunger 1 and the pop out dome are forcing medication into the needle cannula hence into a body; any hydrostatic pressure 10 cause by the thrust of the plunger is essentially equal on all points of the dome and the pop out dome and the shape of the pop out dome remains unchanged and all forces are essentially evenly distributed through the pop out dome and into the dome foundation. When a concentrated load is applied to parts of the pop out dome, the pop out dome will start to deflect in the area of the applied concentrated load.

Referring to FIG. 12 there is shown a section elevation view of the pop out dome 21 as it will look as the base plate 14 exerts a concentrated load on the pop out dome 21. The pop out dome 21 will start to deflect and as the concentrated load is continued, the pop out dome start to form a reverse dome 30.

Referring to FIG. 12A there is shown another section elevation similar to FIG. 5 showing the dome flange 27 inside of the dome notch 26 that is formed in the dome foundation 20.

As the pop out dome 21 is forced into a reverse dome, the dome flange will start to rotate about the dome trunnion 28 and will further start to withdraw from the dome notch 26.

Referring to section 12B there is shown an enlarged section elevation of the pop out dome 21 forming into a reverse dome 30.

The dome trunnion 28 has rotated about the proximal end of the dome foundation 20 causing the dome flange 27 to be withdrawn from the dome notch 26 and further causing the dome flange to reverse its configuration wherein it will unable to catch onto or into the dome notch.

Referring to FIG. 12C there is shown an enlarged section elevation of the complete reversal of the pop out dome 21.

The dome trunnion 28 has been forced completely past the proximal end of the dome foundation 20 and cannot grasp or even touch the inside wall of the dome support means 19 because the dome support means has a greater inside diameter than the outside diameter of the pop out dome reversed or the reversed dome 30 and a greater outside diameter of the dome trunnion; at this moment, the base plate is thrusting into the pop out dome by the biased spring.

Referring to FIG. 13 there is shown a section elevation of the pop out dome 21 formed into a completely reversed dome 30 and in a instant the pop out dome will be thrust away from the distal end of the dome support means 19.

Referring to FIG. 14 there is shown a section elevation of the pop out dome 21 and now the reversed dome being thrust from the dome support means 19.

Figure 15:
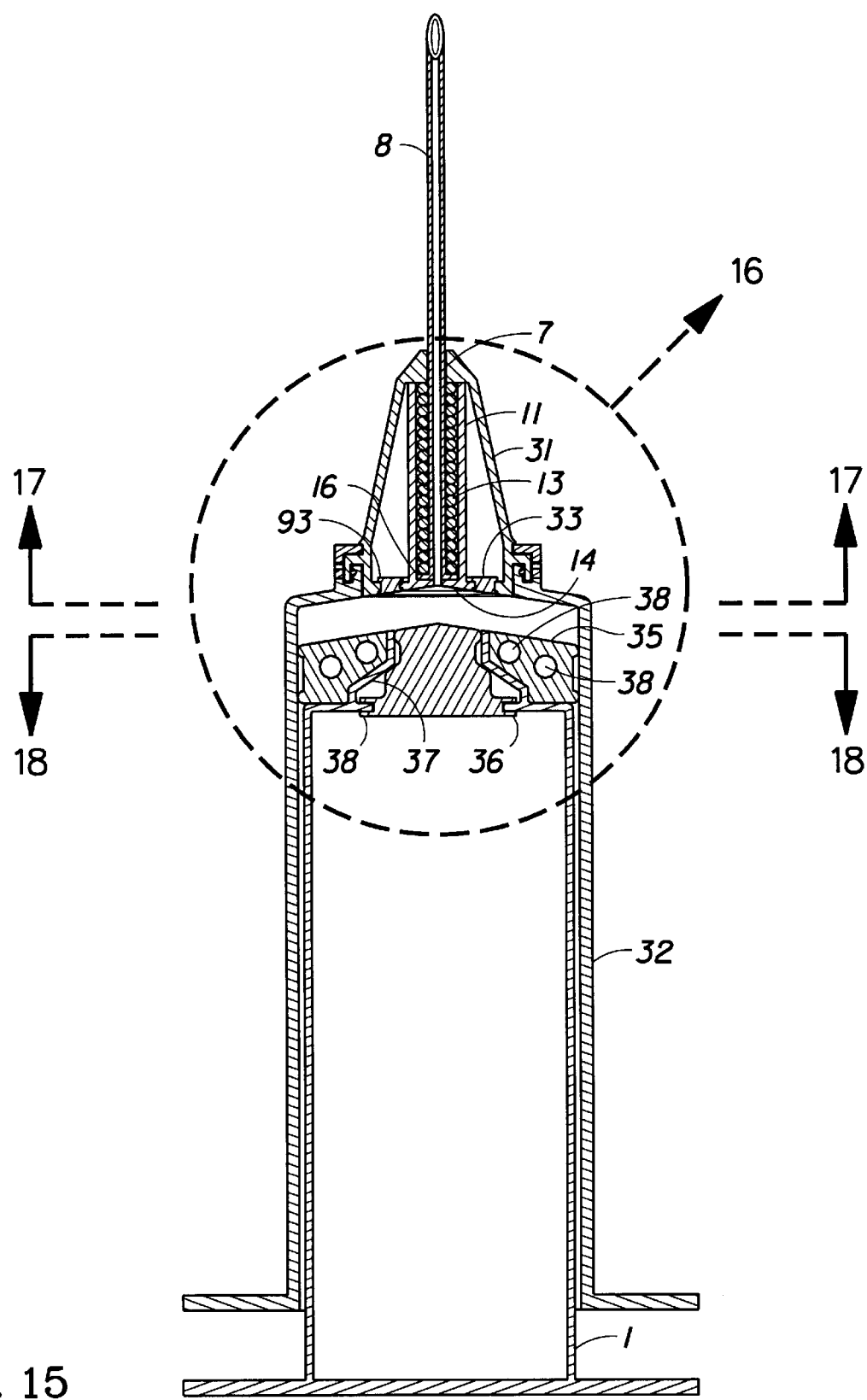
FIG. 15 is a section elevation of the second preferred embodiment of the snap on safety needle module and the pop out plunger plug.

Referring to FIG. 15 there is shown a section elevation of the second preferred embodiment of the present invention.

A snap on needle cannula module 31 is shown suitably fixed to the snap on syringe module 32. The needle cannula 8 is shown as the same needle cannula in the first preferred embodiment. A biased spring 13 is shown disposed about the needle cannula and the spring shield 11 10 is shown disposed about the biased spring. The needle base plate 16 is shown fixed to the proximal end of the needle cannula and the base plate 14 is shown at the proximal end of the needle base plate. The H retaining ring 33 is shown retaining the base plate and the biased spring 13.

The distal end of the plunger 1 is shown with a plunger flange 36 and the plug support means 37 is shown fixed to the distal end of the plunger flange. The compressible plunger seal 35 is shown with compression chambers 38. The compressor chambers are designed to allow the compressible plunger seal to compress as will be shown in FIG. 20.

Figure 16:
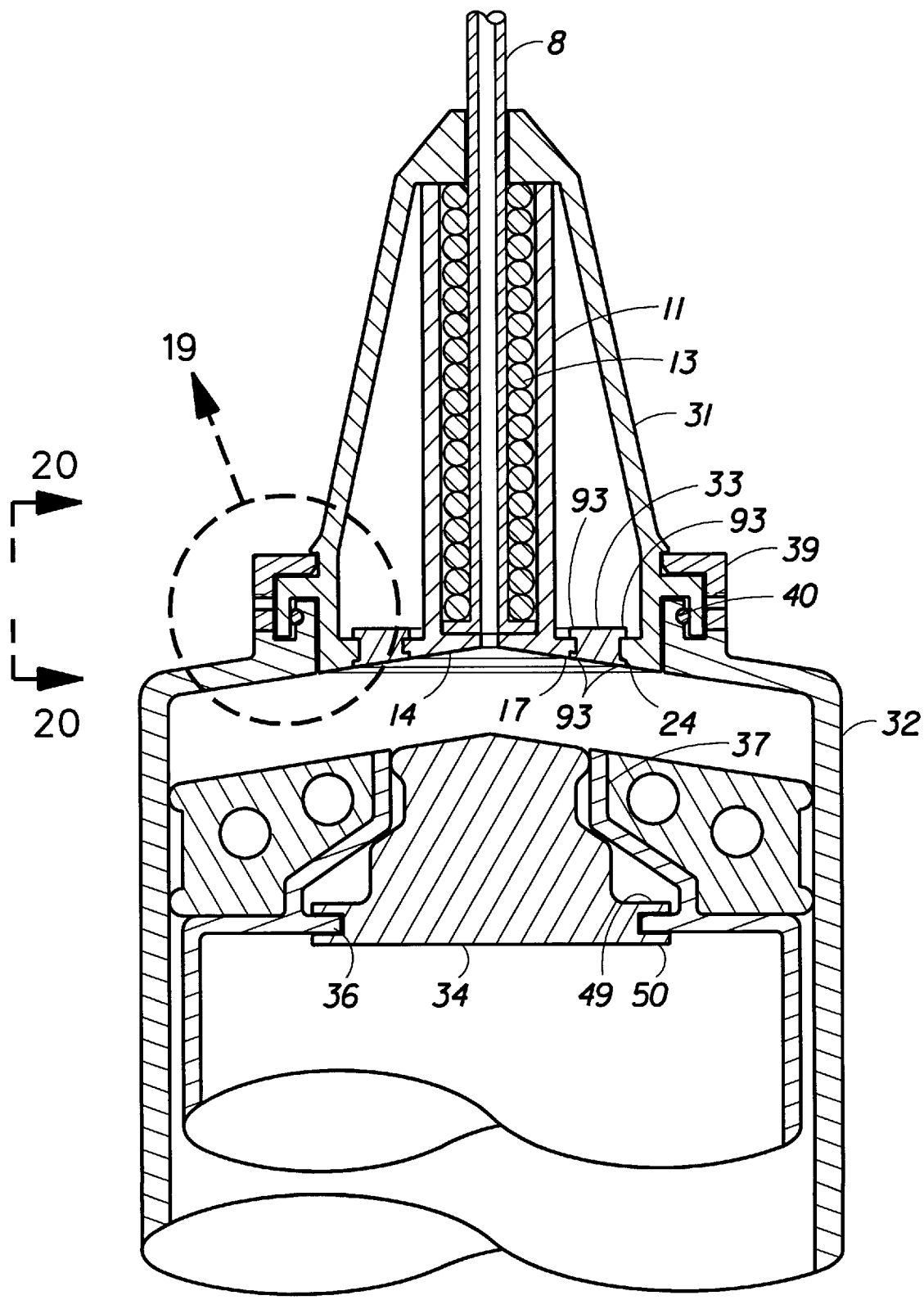
FIG. 16 is an enlarged section elevation of the snap on safety needle cannula module and the pop out safety plunger plug.

Referring to FIG. 16 there is shown an enlarged section elevation of the second preferred embodiment.

The snap on syringe module 32 is shown fastened to the snap on needle cannula module 31 by the snap ring 39. An O ring 40 is shown forming a fluid tight and gas tight connection between the snap on needle cannula module and the snap on syringe module. The H retaining ring 41 is shown fixed to the module flange 24 and the base plate flange 17 wherein each leg 93 of the H retaining ring laps over each side of the inner periphery of the modular flange 24 and each side of the outer periphery of the base plate flange 17 forming a fluid tight and gas tight connection.

The double flange plug 34 is shown forming a fluid tight and gas tight connection between the inner surface of the plug support means 37 and the double flange plug. The upper flange 49 and the lower flange 50 are shown holding the double flange plug to the plunger flange 36. Although there are two flanges shown in this figure, the upper flange is most necessary and the lower flange could be eliminated.

Figure 17:
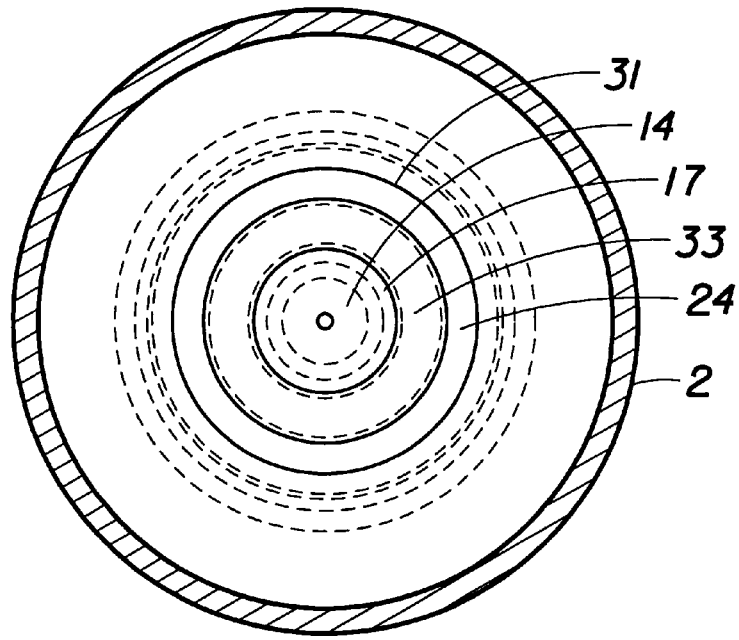
FIG. 17 is a section plan view of the needle and base plate.

Referring to FIG. 17 there is shown a section plan view of the base plate 14 as taken through FIG. 16.

The base plate 14 is at the center of the snap on needle cannula module 31 however it could be offset also or near one side of the safety syringe 2. The H retaining ring 41 is shown fixed to the module flange 24 and the base plate flange 17.

Figure 18:
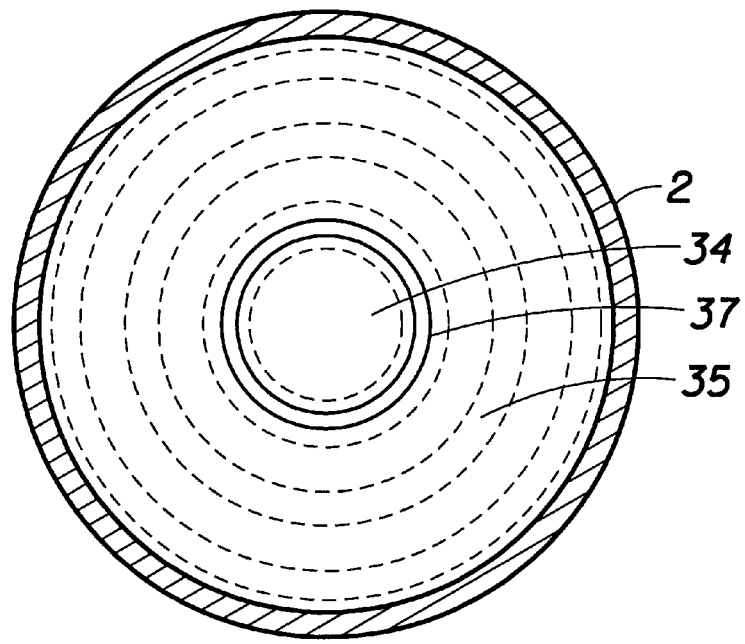
FIG. 18 is a section plan view of the pop out safety plunger plug inside the plunger.

Referring to FIG. 18 there is shown a section plan view of the double flange plug 35 as taken through FIG. 15.

The plug support means 37 is shown supporting the double flange plug 34. The compressible plunger seal 35 is shown on the inside surface of the syringe module 2.

Figure 19:
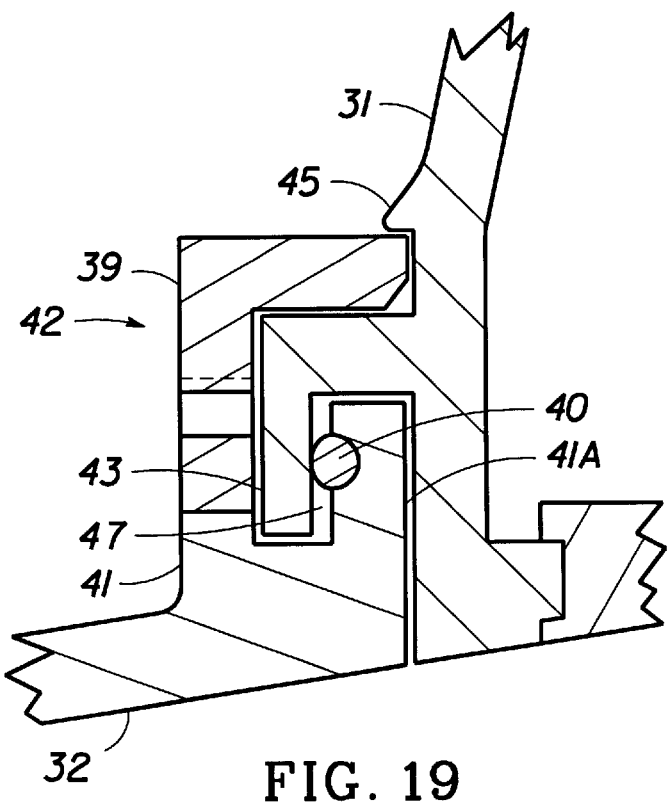
FIG. 19 is an enlarged section elevation view of the snap on device.

Referring to FIG. 19 there is an enlarged section elevation of the snap on means 42 as taken from FIG. 16.

There can be many versions of snap on means and therefor this patent should not be limited to only this version of a snap on means.

The snap on needle cannula module 31 is shown with a module snap on flange 43 that is suitably compressing an O ring 40 to form a fluid tight and gas tight connection. The snap on means 42 operates by placing the module snap on flange 43 into the syringe snap on slot 47; the snap over ring 44 is pulled over the pull over flange 45 and rotated until the snap on lock 48 shown in FIG. 20 locks the snap on needle cannula module 31 to the snap on syringe module 32.

Figure 20:
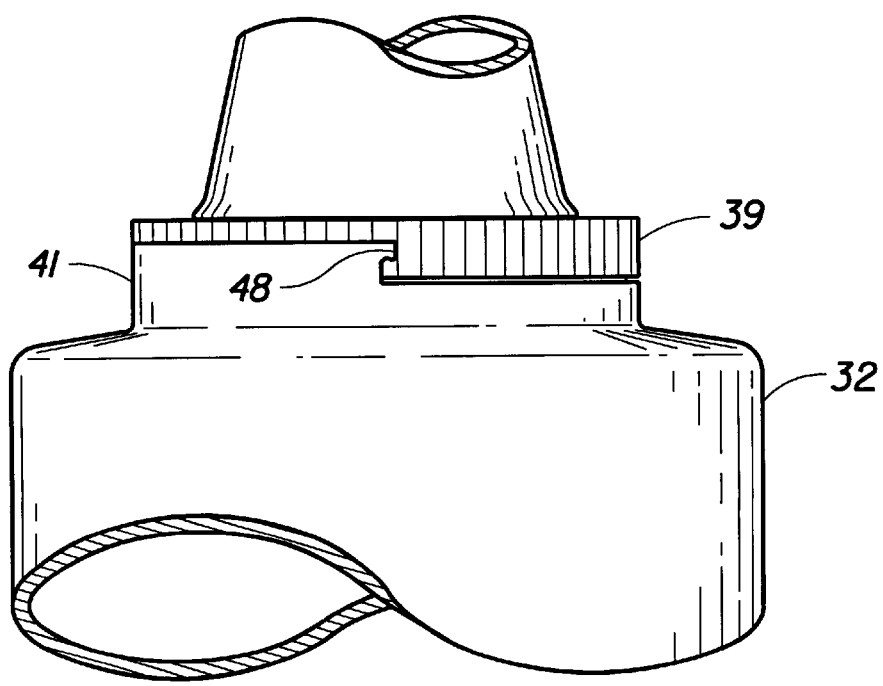
FIG. 20 is an elevation view of the snap on needle cannula module.

Referring to FIG. 20, there is shown an elevation view of the snap on needle cannula module 31 suitably fixed to the snap on syringe module 32 by the snap over ring 44 that is locked in place by the snap on lock 48.

Figure 21:
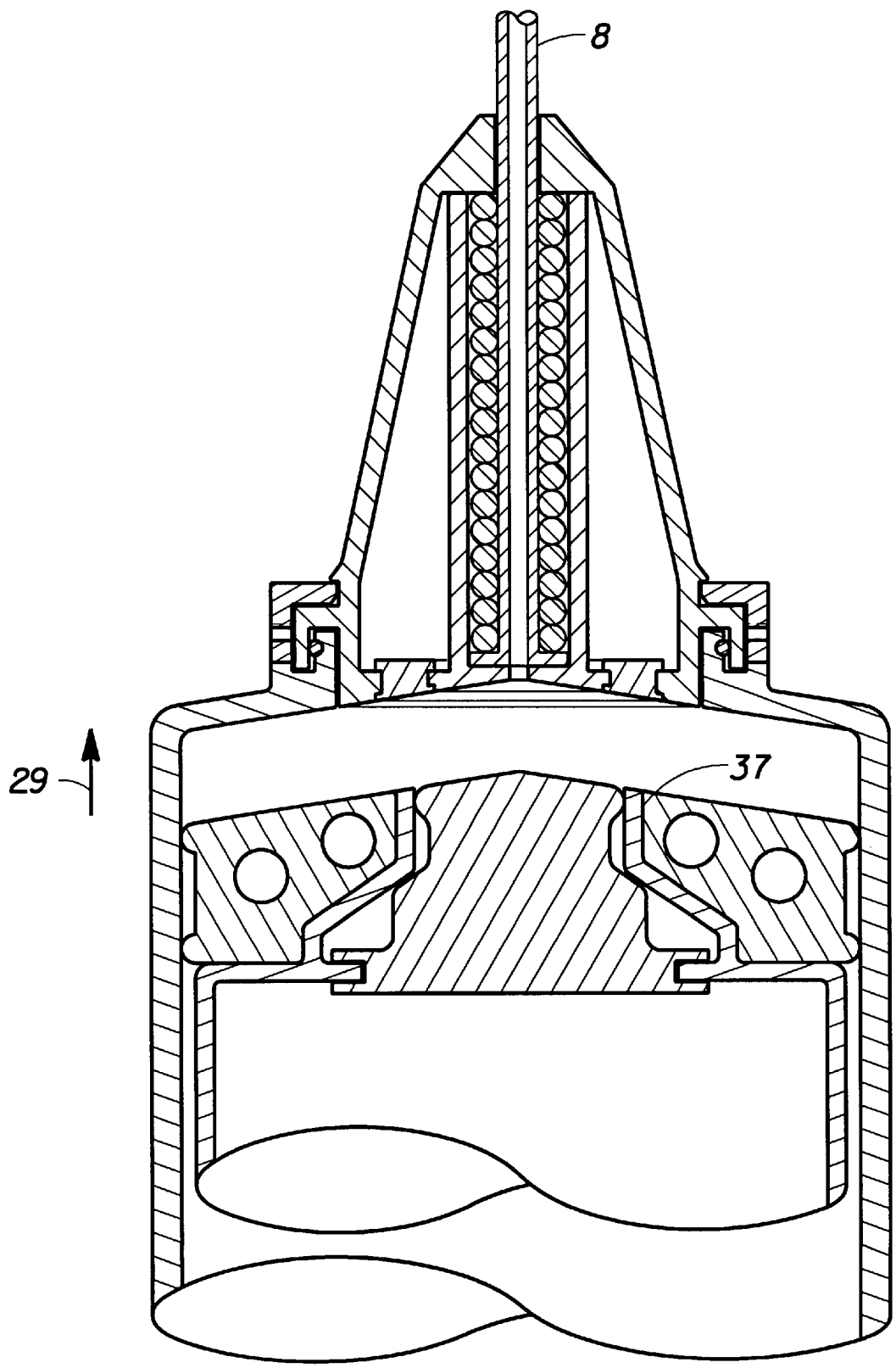
FIG. 21 is an enlarged section elevation view of the plunger plug moving toward the needle cannula.

Referring to FIG. 21 there is shown an enlarged section elevation of the distal end of the plug support means 37 moving in a cannula direction 29.

Medication is flowing under pressure from the syringe module 2 into the needle cannula 8 and into a body not shown in this figure.

Figure 22:
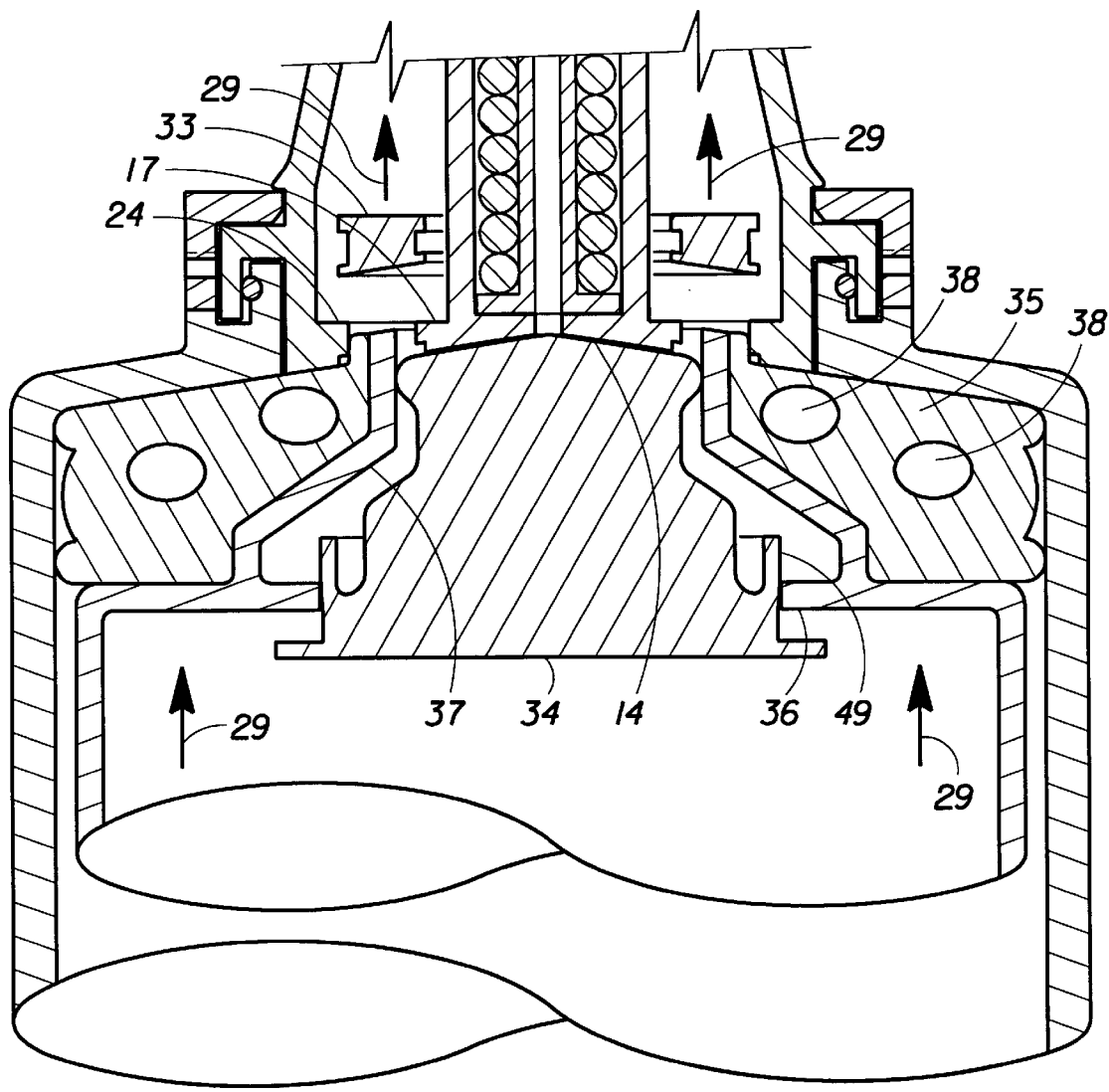
FIG. 22 is an enlarged section elevation view of the plunger module thrusting into the safety needle cannula module.

Referring to FIG. 22 there is shown an enlarged section elevation of the distal end of the plug support means 37 impacting the proximal end of the H retaining ring 41 in a cannula direction 29

The H retaining ring has been dislodged from the base plate flange 17 and the module flange 24 and is now moving in a cannula direction 29. The base plate 14 has also started to dislodge the double flange plug 34 from the plunger flange 36 by bending the upper flange 49 on the plunger flange 36. As the double flange plug is being dislodged. The compressible plunger seal is also being compressed by allowing the compressor chambers 38 to change shape.

Figure 23:
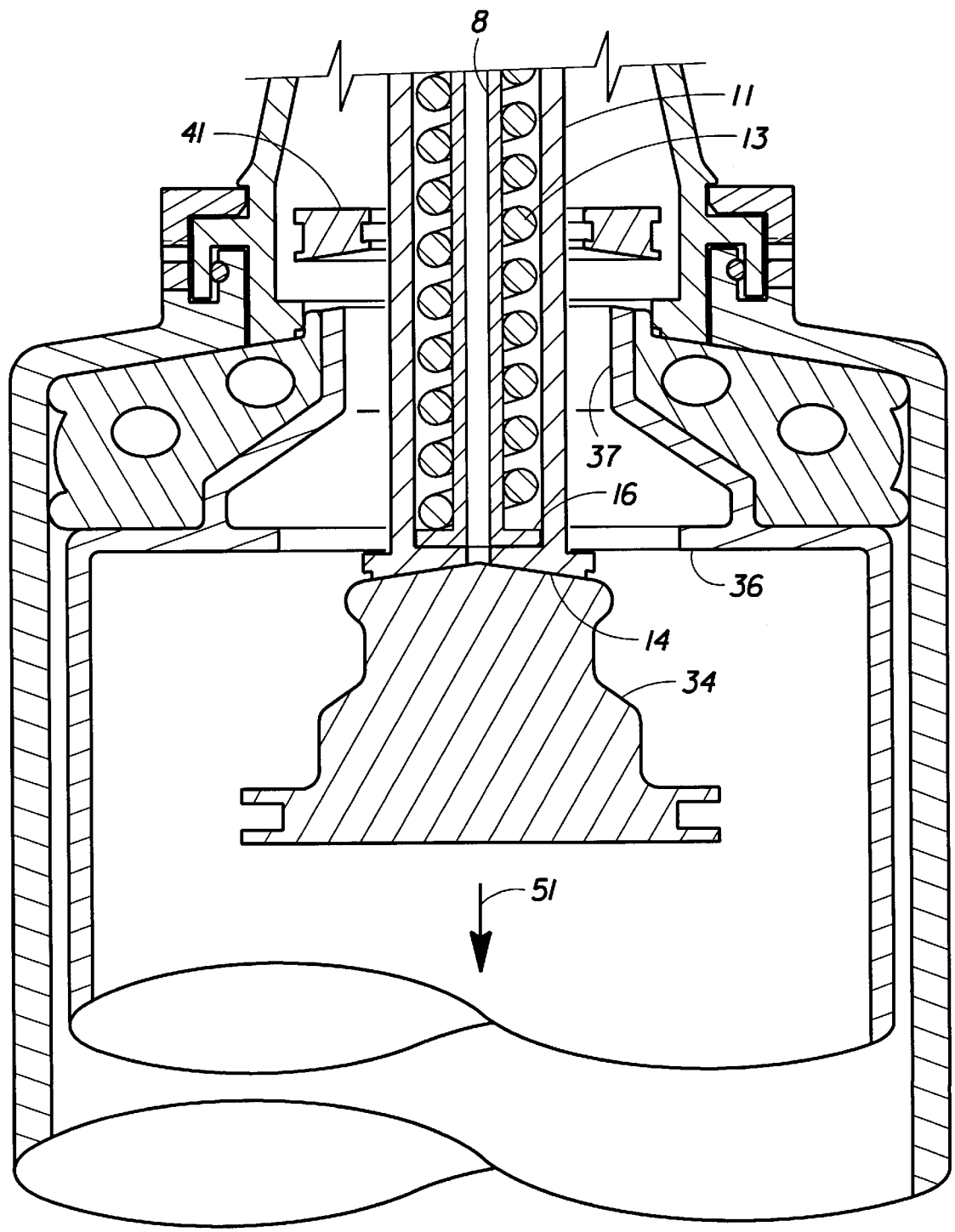
FIG. 23 is an enlarged section view of snap on safety needle cannula module and the needle cannula popping into the plunger module.

Referring to FIG. 23 there is shown a section elevation of the double flange plug 34 being dislodged from the plug support means 37 and the plunger flange 36.

The biased spring 13 is now controlling the movement of the base plate 14, the needle cannula 8 and the needle base plate 16 as the biased spring thrusts the needle cannula in a plunger direction 51. The spring shield 11 is preventing the biased spring from getting caught in the H retaining ring 41.

Figure 24:
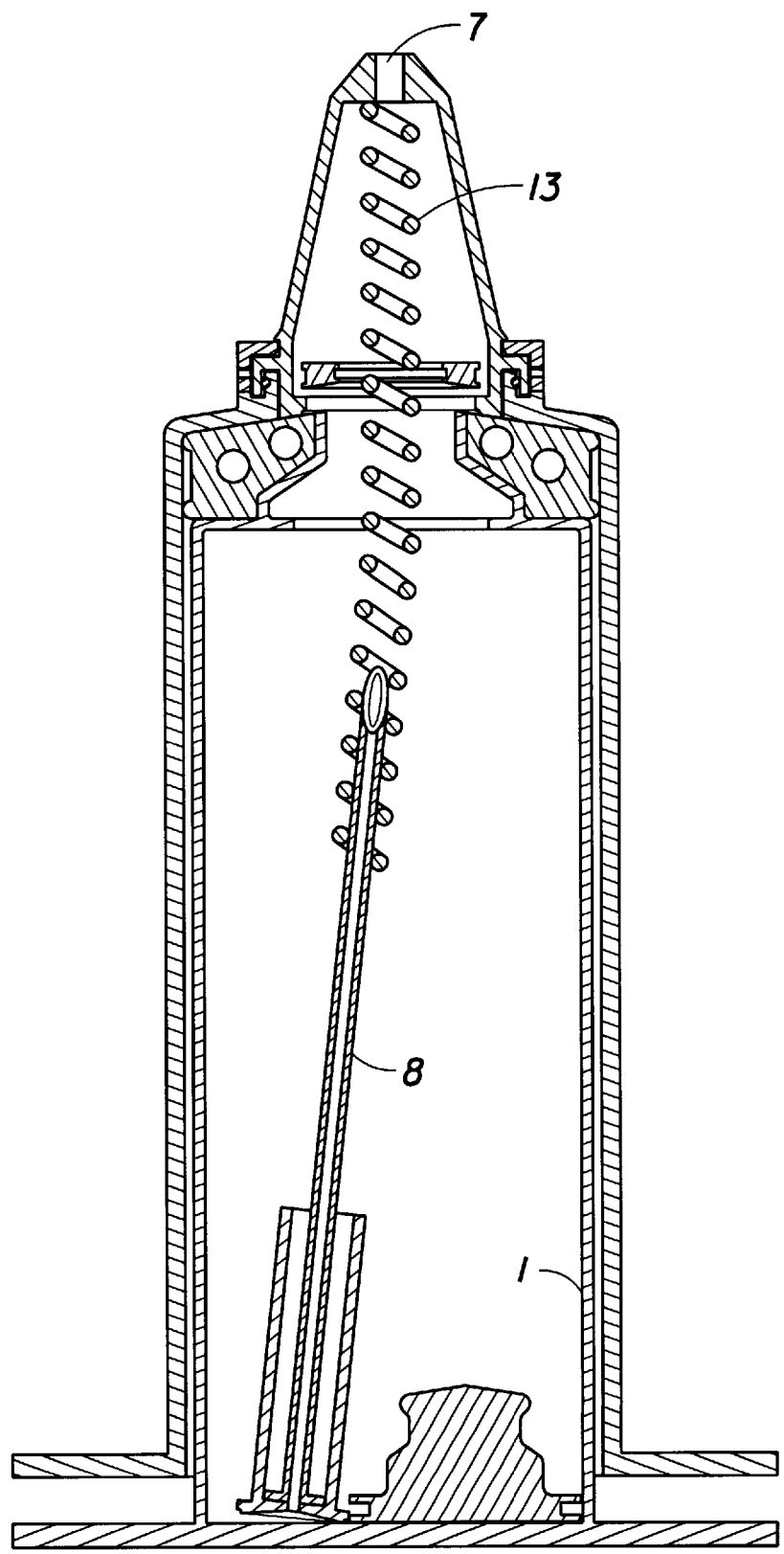
FIG. 24 is a view of the snap on safety needle cannula module with the needle cannula inside of the plunger module.

Referring to FIG. 24 there is shown a section elevation of a disarmed syringe.

The needle cannula 8 is in the hollow plunger 1 and the spring 13 will prevent the needle cannula from re-entering the support tunnel 7.

Figure 25:
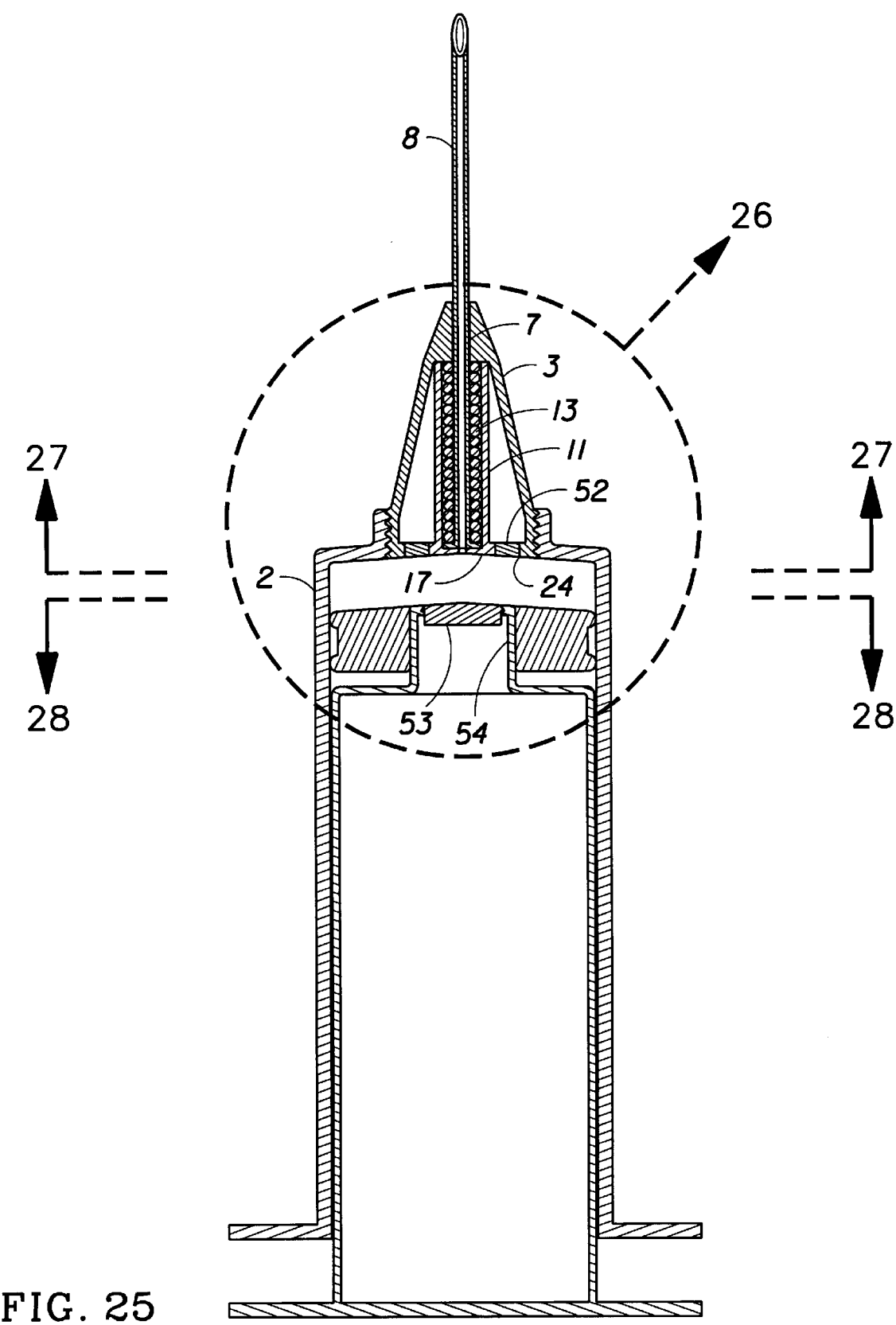
FIG. 25 is a section elevation of the preferred embodiment.

Referring to FIG. 25 there is shown a section elevation of the third preferred embodiment of the present invention.

The safety needle cannula module 3 is shown suitably fixed to the syringe module 2. The needle cannula 8 is shown disposed in the support tunnel 7 and the biased spring 13. The biased spring is shown disposed in the spring shield 11. The friction ring 52 is shown held by friction, adhesive or other bonding means to the base plate flange 17 and the module flange 24.

The plunger barrier 53 is shown suitably fixed to the inside surface of the barrier support 54.

Figure 26:
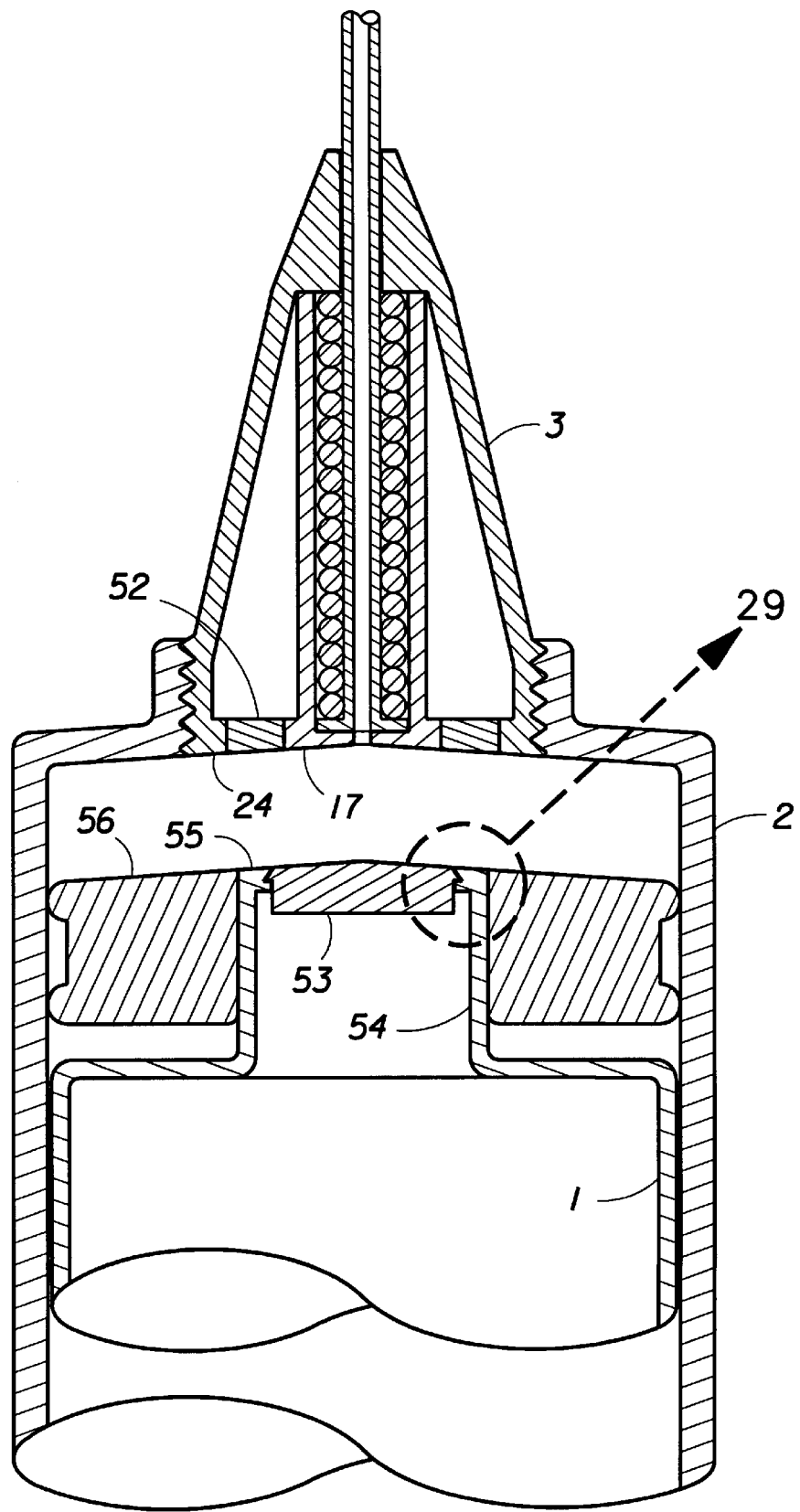
FIG. 26 is an enlarged section elevation of the third preferred embodiment.

Referring to FIG. 26 there is shown an enlarged section elevation of the safety needle cannula module 3, the distal end of the syringe module 2 and the plunger 1 as taken through FIG. 25.

The friction ring 52 is shown suitably disposed between the base plate flange 17 and the module flange 24 and is held in place by friction only; adhesive or other holding means could be used by design choice.

The plunger barrier 53 is shown held to the distal end of the barrier support 54 by a barrier foundation 55. The sliding plunger gasket 56 is shown suitably fixed to the outside surface of the barrier support.

Figure 27:
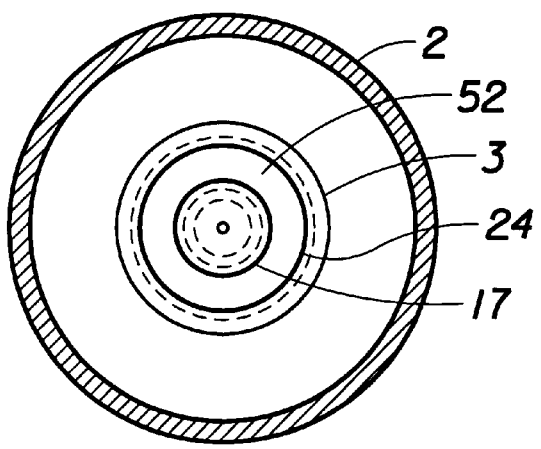
FIG. 27 is a section plan view as taken through FIG. 25.

Referring to FIG. 27 there is shown a section plan view as taken through FIG. 25.

The syringe Module 2 is shown fixed to the safety needle cannula module 3 by threads or other suitable means. The outer diameter of the friction ring 52 is shown fixed to the inside diameter of the module flange 24. The inside diameter of the friction ring 52 is fixed to the outside diameter of the base plate flange 17.

Figure 28:
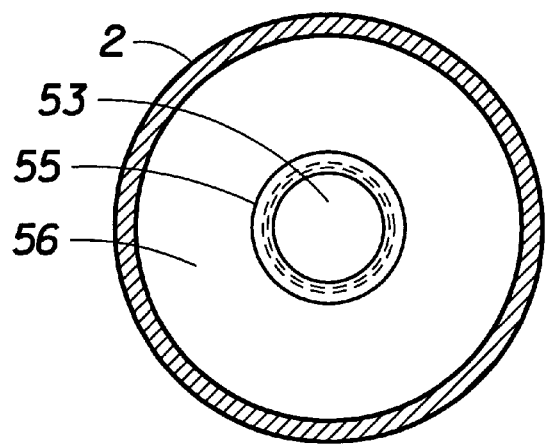
FIG. 28 is a section plan view as taken through FIG. 25.

Referring to FIG. 28 there is shown a section plan view of the distal end of the barrier support as taken through FIG. 25.

The syringe module 2 is shown on the outside diameter and the sliding plunger gasket 56. The distal end of the barrier foundation 55 is shown supporting plunger barrier 53.

Figure 29:
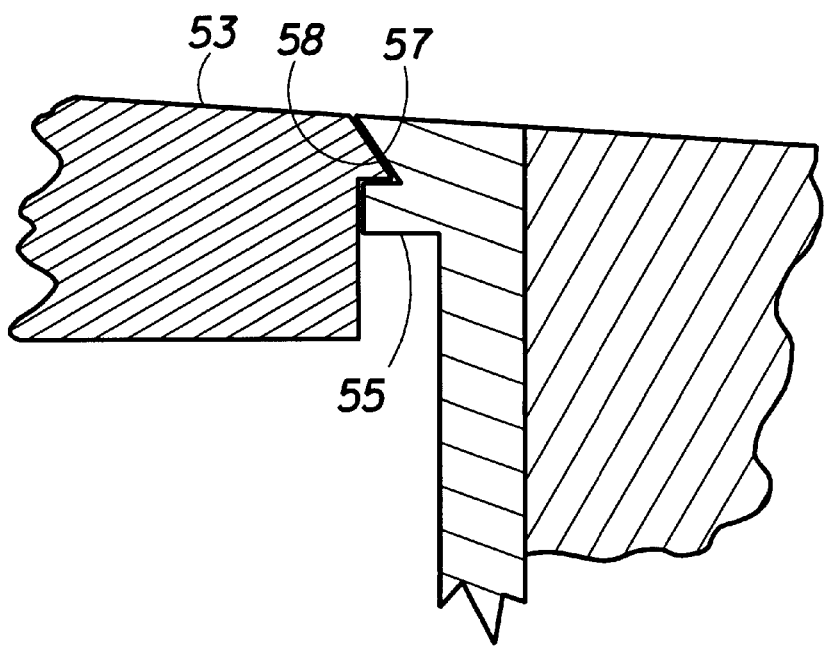
FIG. 29 is an enlarged section elevation as taken through from FIG. 26.

Referring to FIG. 29 there is shown an enlarged section elevation of the barrier foundation 55 supporting the plunger barrier 53 as taken from FIG. 26.

The barrier foundation 55 is shown with a barrier notch 57 that supports the barrier flange 58.

Figure 30:
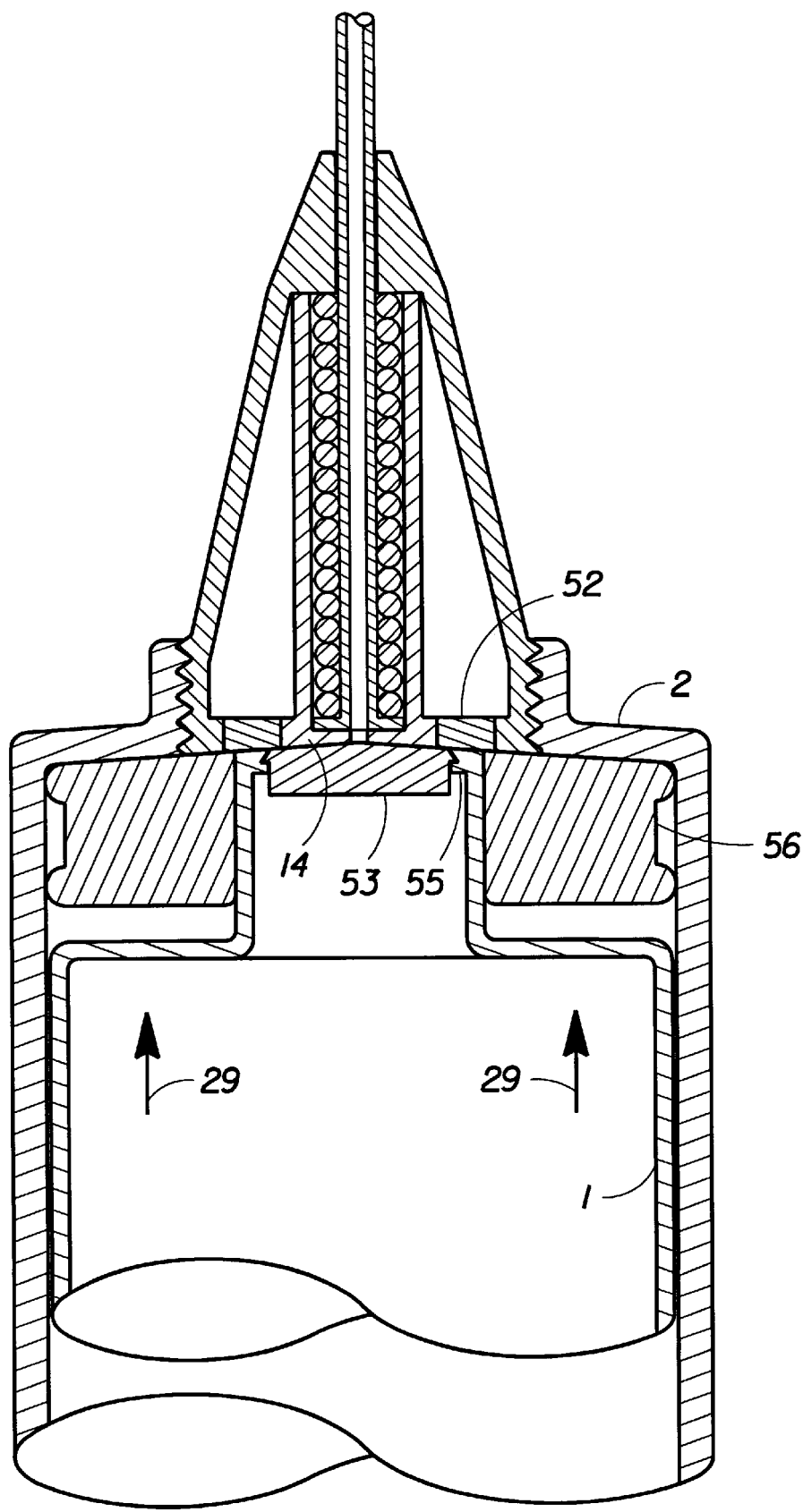
FIG. 30 is an enlarged elevation of the device in operation.

Referring to FIG. 30 there is shown an enlarged section elevation of the plunger 1 moving in a cannula direction 29.

The distal end of the sliding plunger gasket 56 is now in contact with the proximal end of the syringe module 2. The distal end of the barrier foundation 55 is in contact and alignment with the proximal end of the friction ring 52 and the proximal end of the base plate 14 is in engagement with the distal end of the plunger barrier 53.

Figure 31:
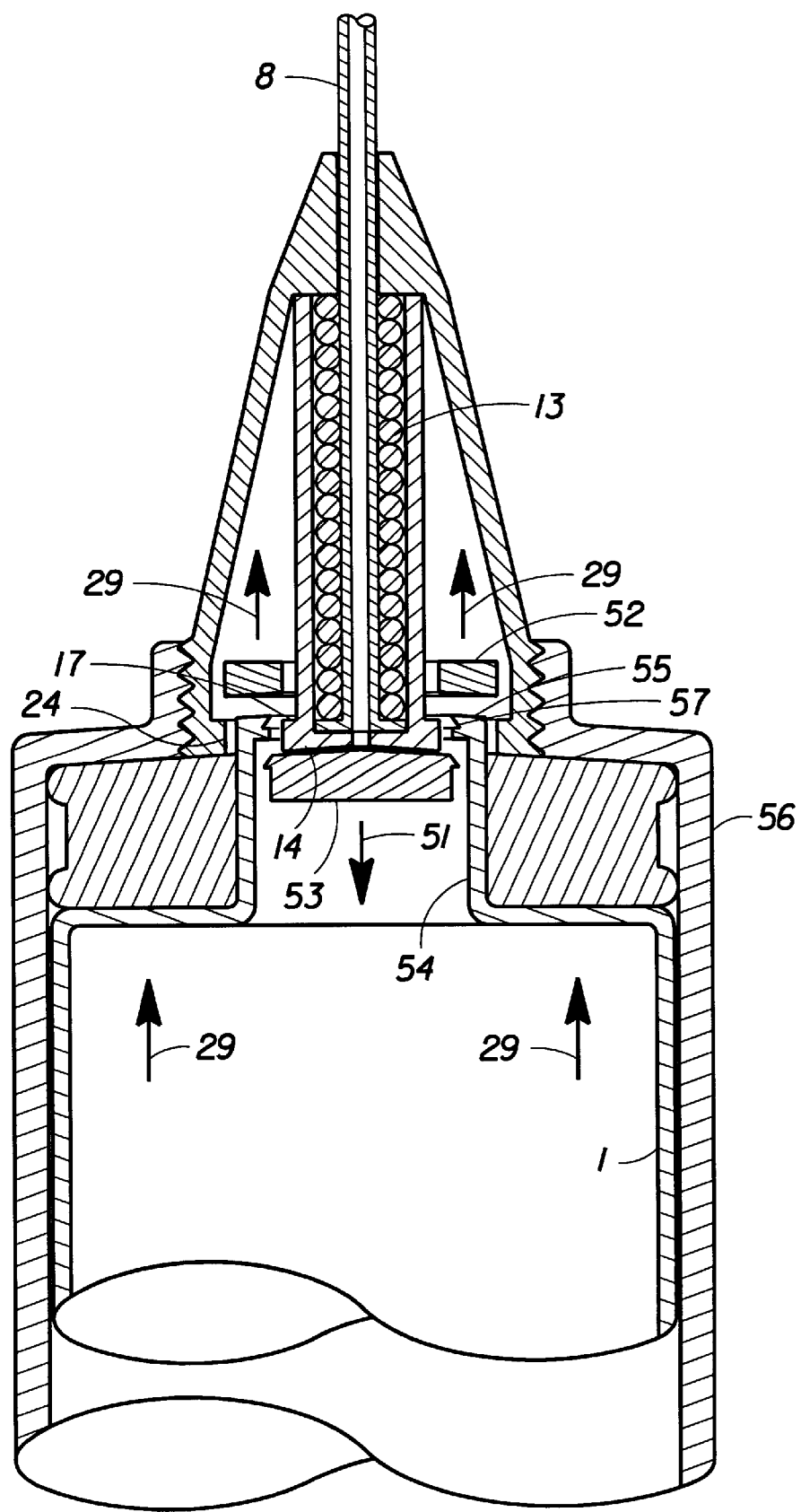
FIG. 31 is a section elevation of the device moving.

Referring to FIG. 31 There is shown a section elevation of the distal end of the barrier foundation 55 and the barrier support moving in a cannula direction 29 wherein the barrier foundation and the barrier support 54 have popped the friction ring 52 off of the base plate flange 17 and the module flange 24. The base plate 14 has also popped the plunger barrier 53 from the barrier notch 57 in the barrier foundation 55. The biased spring 13 is now thrusting the needle cannula 8 and the plunger barrier into the plunger 1 in a plunger direction 51. The sliding plunger gasket 56 is shown having slid down the outer surface of the barrier support.

Figure 32:
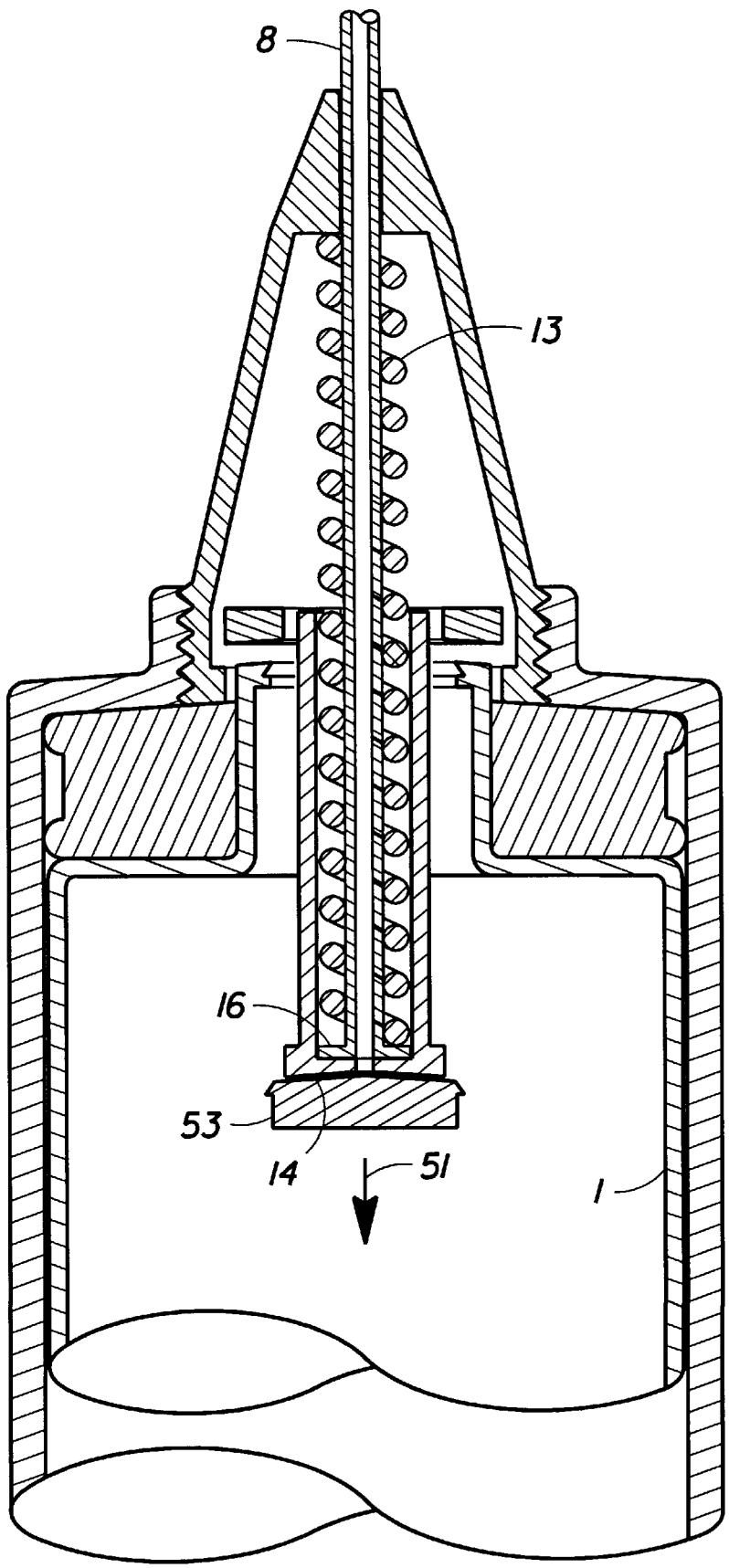
FIG. 32 is a section elevation of the device being broken down.

Referring to FIG. 32 there is shown a section elevation of the biased spring 13 thrusting the plunger barrier 53, the base plate 14, the needle base plate 16, and the needle cannula 8 into the plunger 1 in a plunger direction 51.

Figure 33:
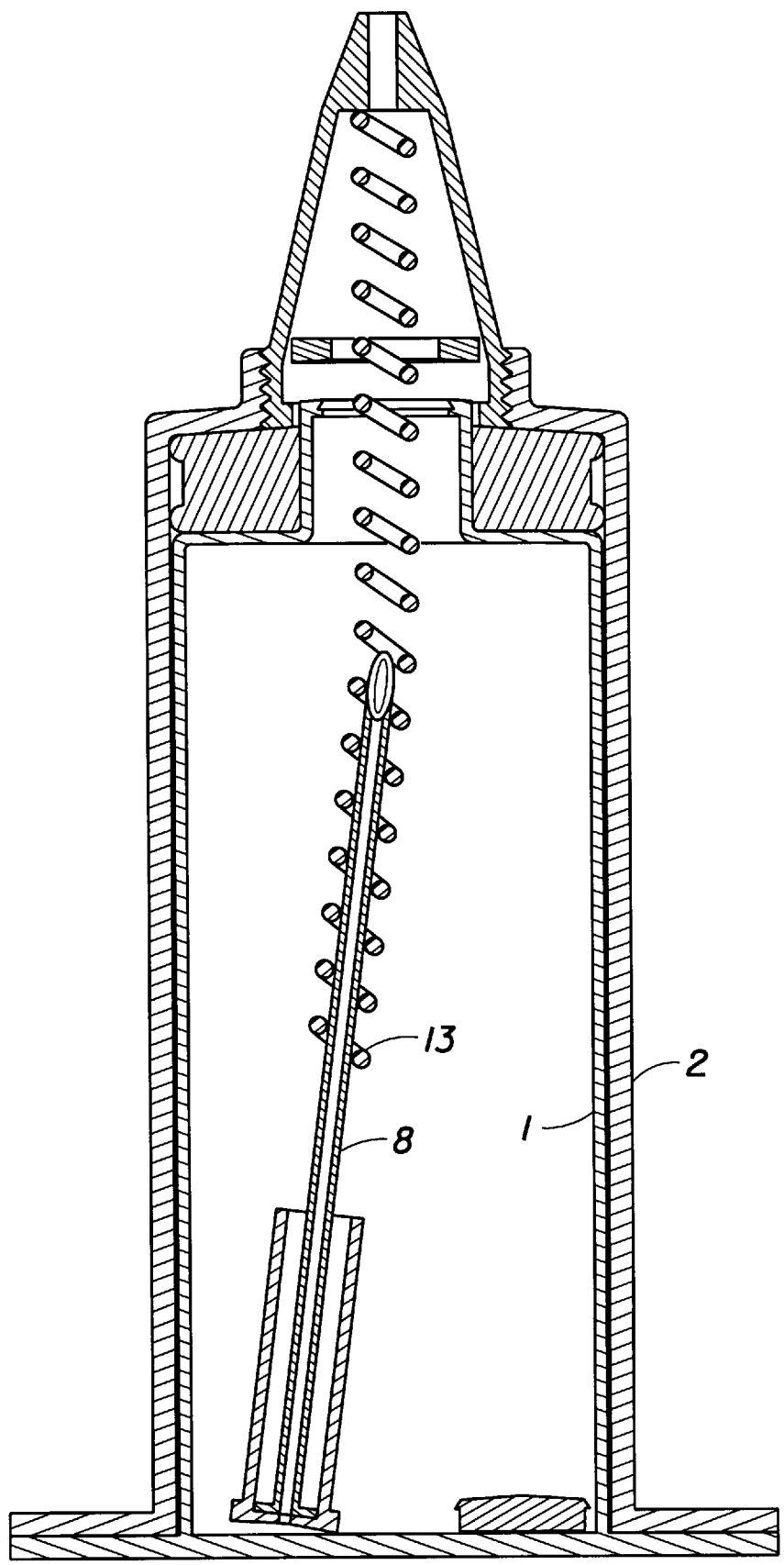
FIG. 33 is a section elevation showing the needle cannula in the syringe and plunger.

Referring to FIG. 33 there is shown a section elevation of the syringe module 2, the plunger 1, and the spring 13 having thrust the needle cannula 8 into the inside of the plunger 1 wherein the needle cannula is trapped and cannot accidentally prick or otherwise injure another.

Figure 34:
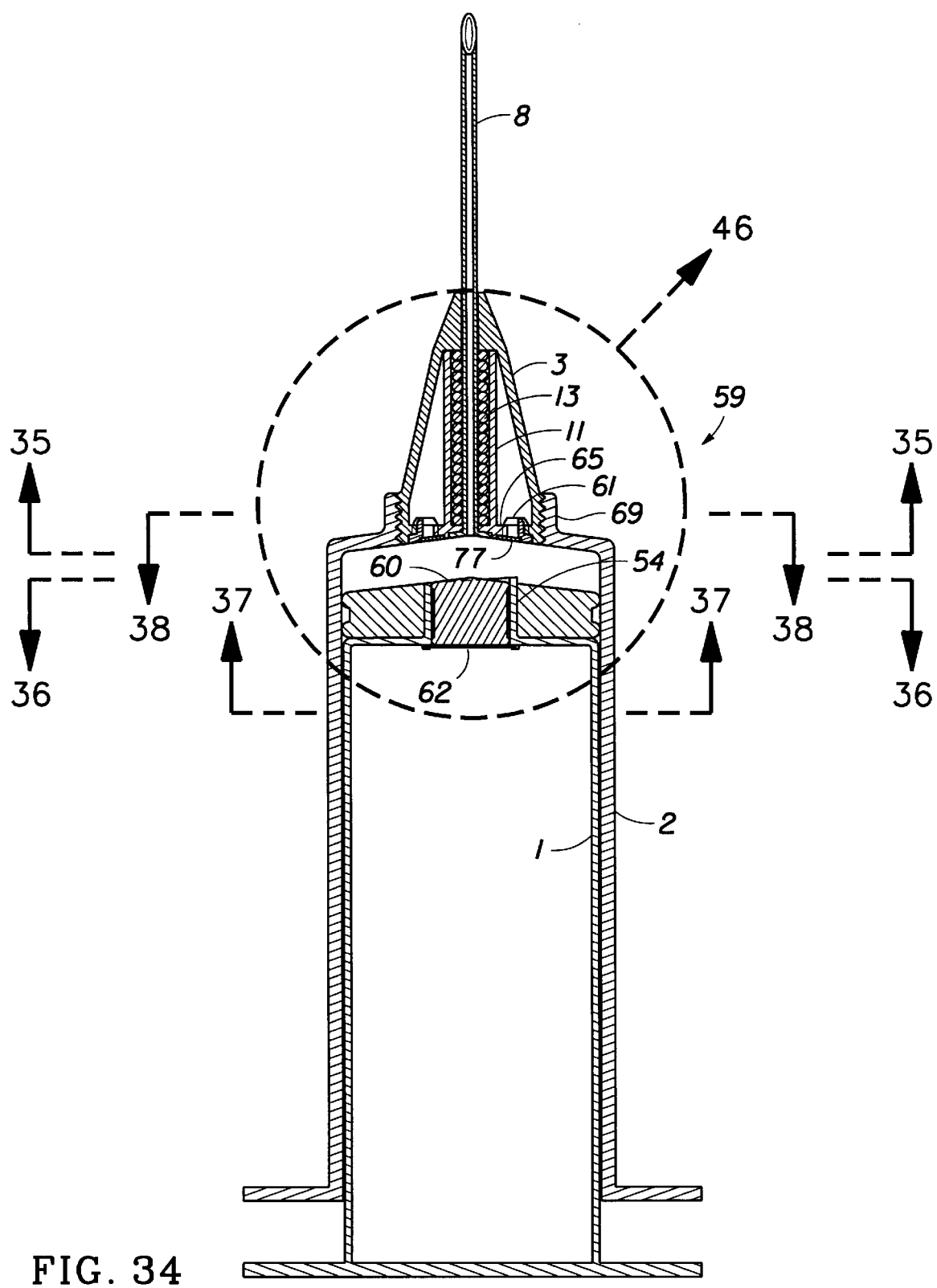
FIG. 34 is a section elevation of the device of the third preferred embodiment.

Referring to FIG. 34 there is shown a section elevation of the modularised safety syringe of the fourth preferred embodiment.

The modularised safety syringe 59 is shown with a needle cannula 8, a plunger 1, a syringe module 2, a biased spring 13, a barrier assembly module 61, a pop out plunger plug 60 in the barrier support 54 and a plug stop 62.

Figure 35:
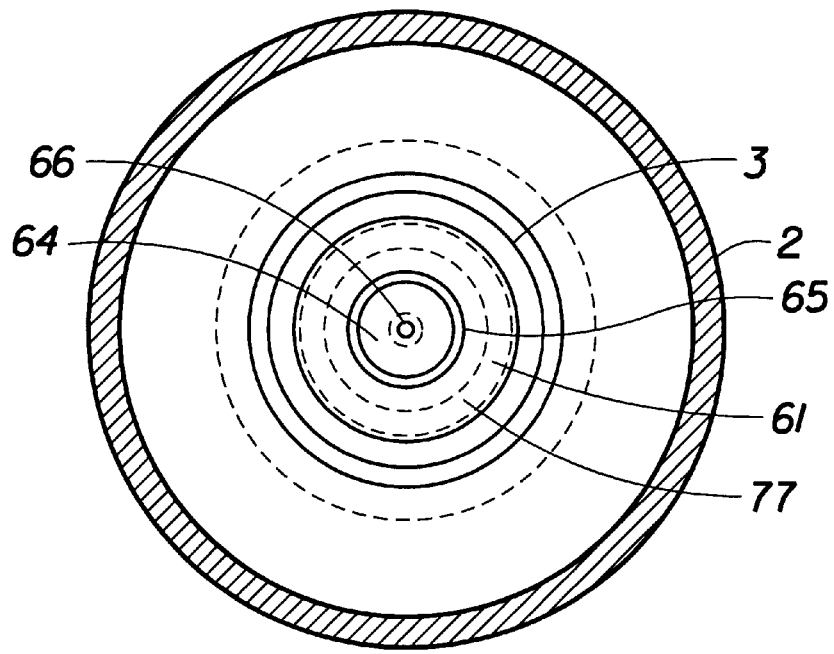
FIG. 35 is a section plan view taken through FIG. 34.

Referring to FIG. 35 there is shown an enlarged section elevation of the modularised safety syringe as taken through from FIG. 34.

The cannula 66 is shown disposed in the support tunnel 7 and having a cone flange 64 at the proximal end.

Referring to FIG. 35 there is shown a section plan view of the syringe module 2, the safety needle cannula module 3 and the barrier assembly module 61.

The cannula 66 is shown in the center of the barrier assembly module and cone flange 64.

Figure 36:
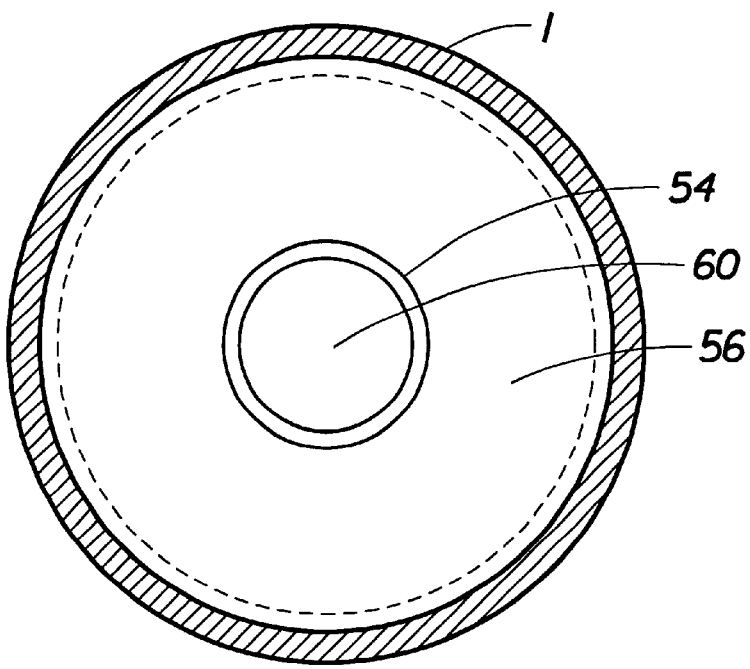
FIG. 36 is a section plan view taken through FIG. 34.

Referring to FIG. 36 there is shown a section plan view of the barrier support 54, the sliding plunger gasket 56 and the pop out plunger plug 60 as taken through FIG. 34.

The sliding plunger gasket is on the inside surface of the plunger 1.

Figure 37:
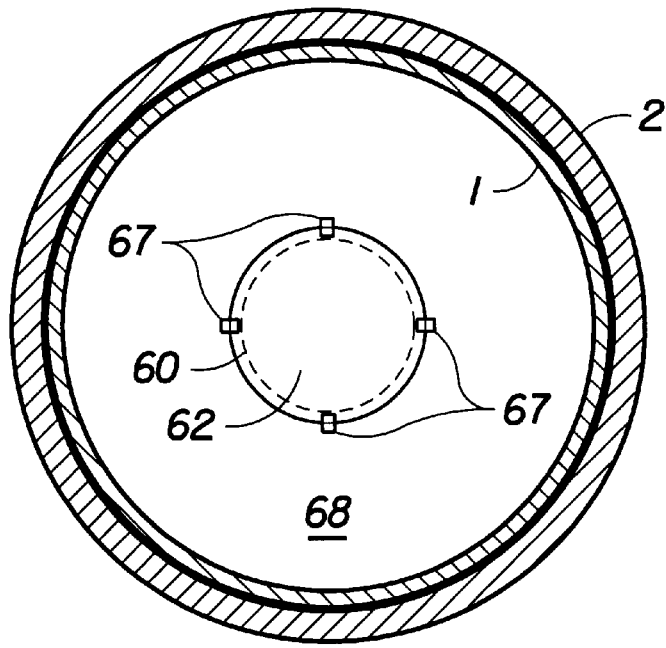
FIG. 37 is a section plan view taken through FIG. 34.

Referring to FIG. 37 there is shown a section elevation of the proximal end of the pop out plunger plug 60 being held in place by the plug stop 62 as taken through FIG. 34.

The plug stop 62 is held in place by the break away tabs 67 that are suitably fixed to the distal plate 68 at the distal end of the plunger 1. The plunger 1 is shown in the inside surface of the syringe module 2.

Figure 38:
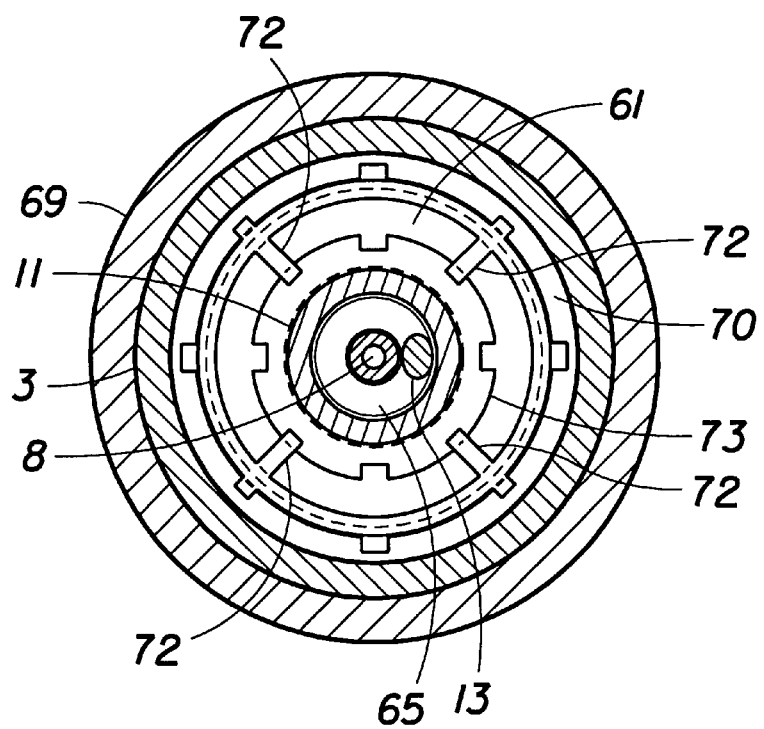
FIG. 38 is a section plan view taken through FIG. 34.

Referring to FIG. 38 there is shown a section elevation plan view of the barrier assembly module 61 in the safety needle cannula module 3 and the syringe extension 69.

The barrier assembly is held in place or is fixed to the safety needle cannula module 3 on the module flange 70 that is formed on the inside and proximal end of the safety needle cannula module. The barrier assembly is held in place and is supported by the inner tabs 72 latching onto the module flange 70 and the outer tabs 72 locking onto the support flange 73. The support flange is formed at the proximal end of the spring shield 11. The needle cannula 8 is shown in the center.

Figure 39:
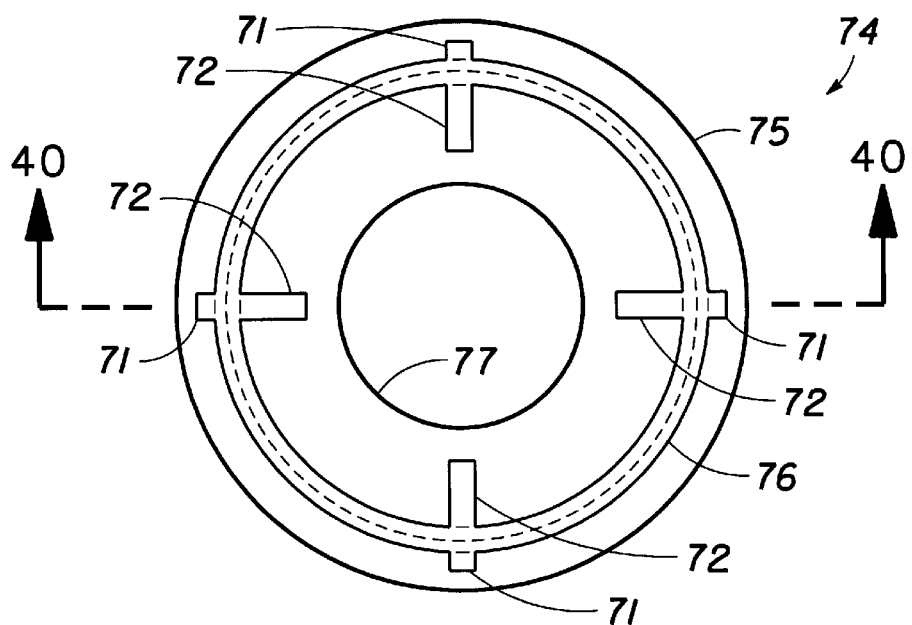
FIG. 39 is a plan view of the tab ring.

Referring to FIG. 39 there is shown a plan view of the tab ring 74.

The tab ring has a ring flange 75 on the outer periphery and a tab support ring 76 with outer tabs 71 on the inside of the tab support ring. Inner tabs 72 are shown fixed to the inside surface of the tab support ring. A frangible ring 77 is also shown fixed to the inside diameter of the tab ring. Although four inner tabs and four outer tabs are shown there could be as few as one inner tab and one outer tab by design choice or there could also be more than four inner tabs or four outer tabs by design choice.

Figure 40:
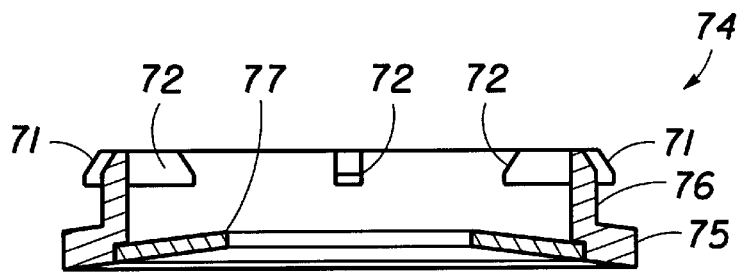

Referring to FIG. 40 there is shown a section elevation of the tab ring 74 as taken through FIG. 39.

The ring flange 75 is shown formed on the tab support ring 76. The inner tabs 72 are shown formed on the inside surface of the tab ring and the outer tabs 71 are shown formed on the outside surface of the tab ring. The frangible ring 77 is shown suitably fixed to the tab ring 74 by adhesive, friction, or other bonding means by design choice. The frangible ring is designed to break under various design loading or specific concentrated loads by design choice. The ring flange 75 is shown forming the outer periphery of the tab ring.

Figure 41:
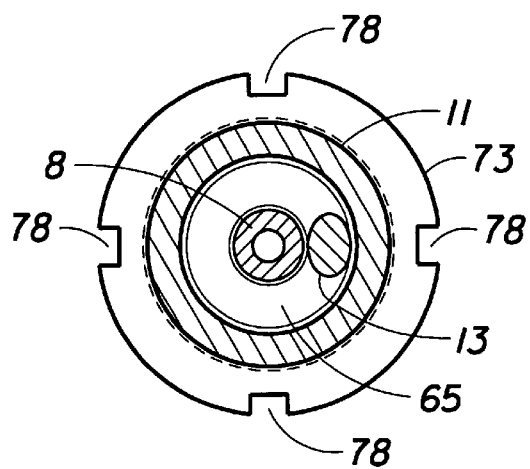
FIG. 41 is a plan view of the support flange.

Referring to FIG. 41 there is shown a plan view of the support flange 73.

The support flange is shown with support flange slots 78 formed on the outer periphery of the support flange. The support 10 flange slots are located to correspond with the inner tabs of the tab ring. The spring shield 11 is shown fixed to the support flange and the needle cannula 8 is shown at the center of the support flange.

Figure 42:
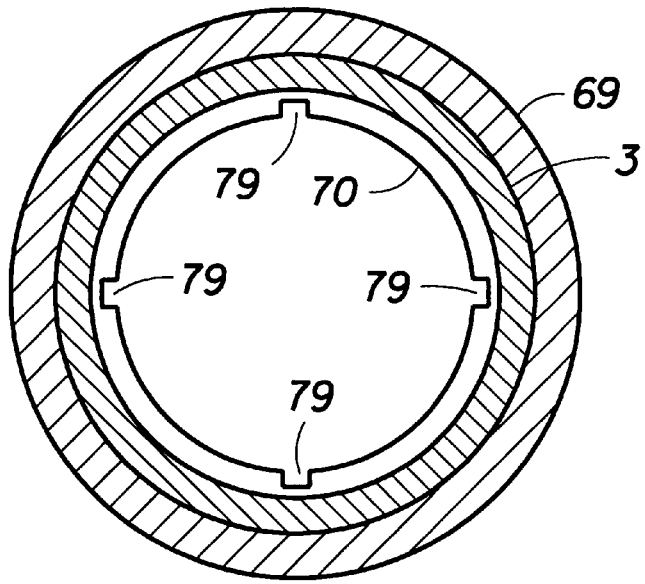
FIG. 42 is a section plan view of the module flange.

Referring to FIG. 42 there is shown a section plan view of the module flange 70 of the safety needle cannula module 3 that is in the syringe extension 69.

The module slots 79 are formed in the module flange 70 to correspond with the location of the inner tabs formed on the tab ring.

Figure 43:
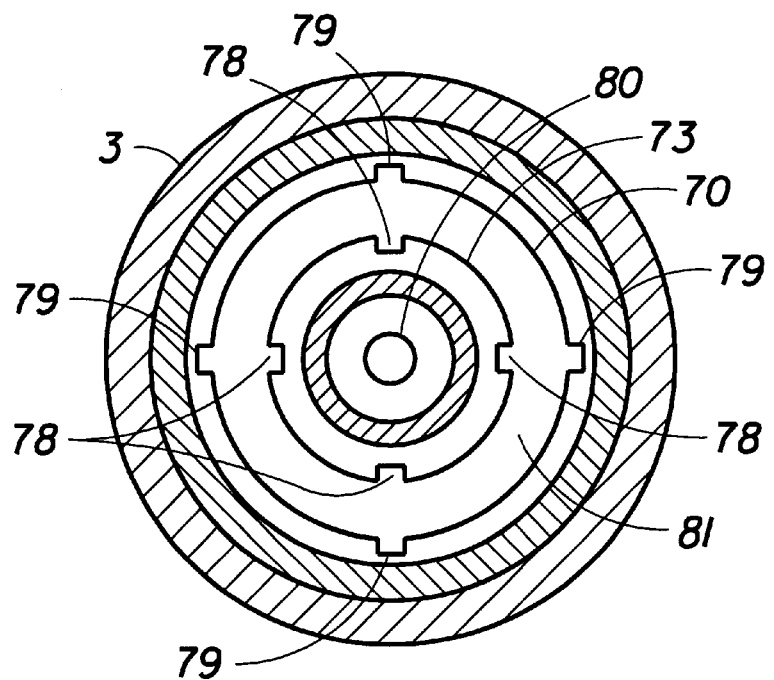
FIG. 43 is a section plan view of the support flange.

Referring to FIG. 43 there is shown a section plan view of the support flange 73 inside of the module flange 70.

The support flange slots 78 are shown in alignment with the module slots 79. Although the support flange slots 78 are shown in alignment with the module slots in this view, this condition is not necessary so long as the slota are in alignment with the inner tabs and outer tab ring.

The safety needle cannula module 3 is shown near the outside and the needle cannula hole 80 is shown on the inside. An annulus 81 is shown formed between the module flange 70 and the support flange 73.

Figure 44:
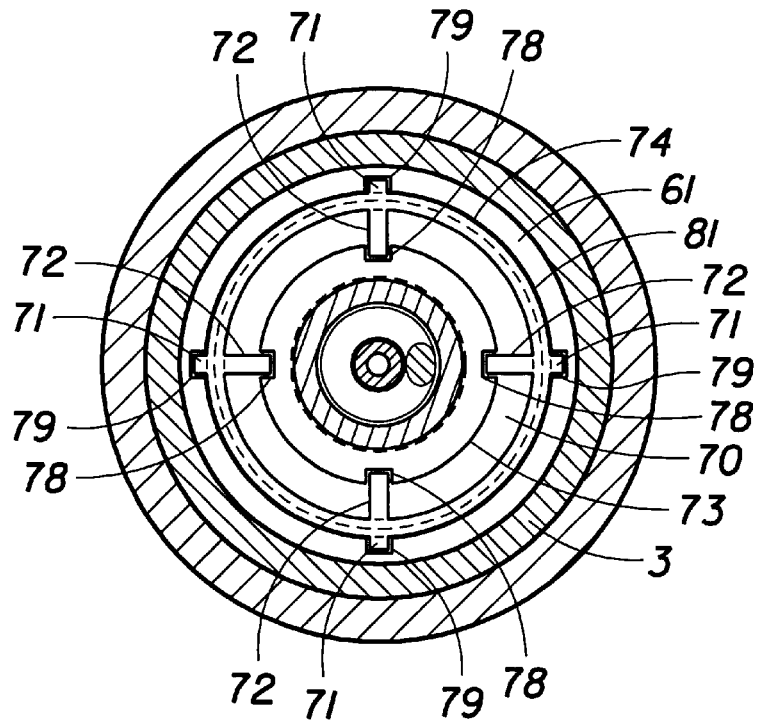
FIG. 44 is a section plan view of the barrier assembly.

Referring to FIG. 44 there is shown a section plan view of the barrier assembly module 61 being assembled to the safety needle cannula module 3.

The tab ring 74 has been inserted into the annulus 81 formed between the module flange 70 and the support flange 73. The inner tabs 72 are in the support flange slots 78 and the outer tabs 71 are in the module slots 79 and the inner tabs and outer tabs are pushed through the flange slots and the module slots.

Figure 45:
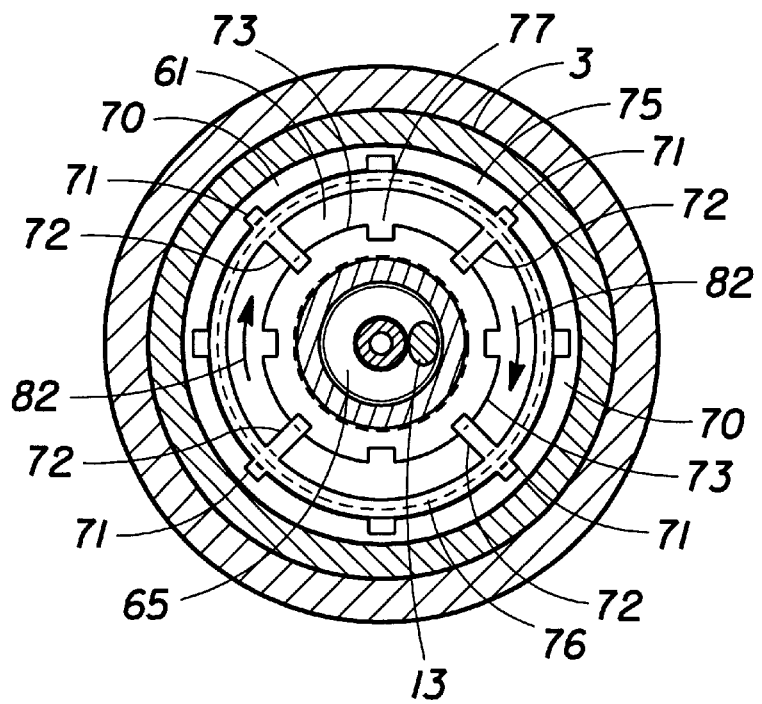
FIG. 45 is a section plan view of barrier assembly rotated.

Referring to FIG. 45 there is shown a section plan view of the barrier assembly module 61 being fixed to the module flange 70 of the 5 safety needle cannula module 3.

As shown in FIG. 44 the tabs have been inserted in the slots and now the tab support ring 76 has been rotated 82 where in the support flange 73 is locked between the inner tabs 72 and the frangible ring 77 and the module flange 70 is locked between the outer tabs 71 and the ring flange 75 thereby forming a fluid tight and gas tight connection between the safety needle cannula module 3 and the barrier assembly module 61. The various flanges have covered the slots thereby making the areas around the slot fluid tight and gas tight. Adhesive or other holding means may be applied to this area also.

Figure 46:
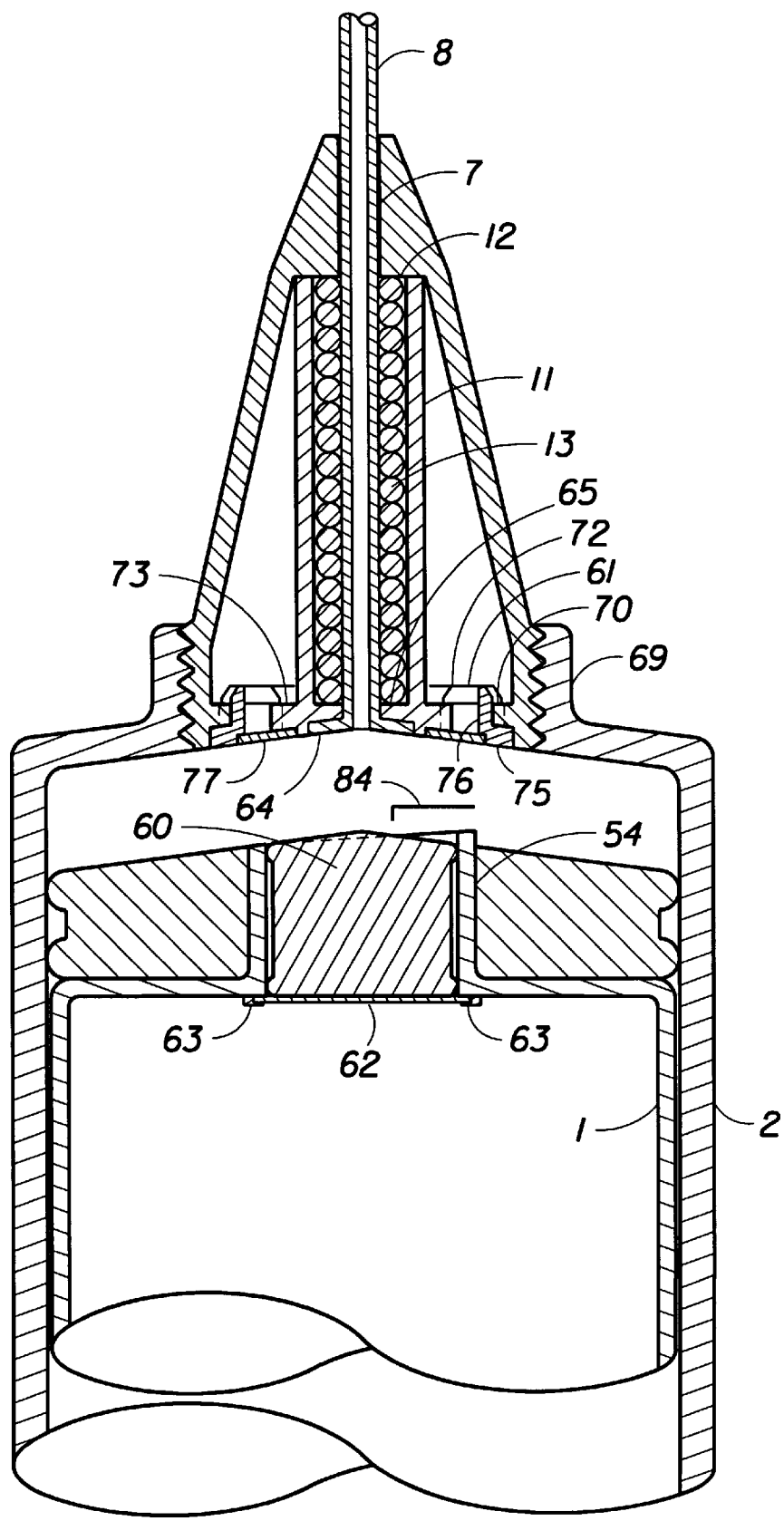
FIG. 46 is an elongated section elevation of the modularised safety syringe as taken through FIG. 34.

Referring to FIG. 46 there is shown an elongated section elevation of the modularised safety syringe as taken through FIG. 34.

The needle cannula 8 is shown disposed in the support tunnel 7. A cone flange 64 is shown fixed to the proximal end of the needle cannula 8. The distal end of the biased spring 13 is thrusting on the cannula flat 12 and the proximal end of the biased spring is shown thrusting on the distal end if the spring foundation 65. The barrier module 61 is restraining the biased spring from thrusting the needle cannula into the syringe module 2 or plunger 1.

The pop out plunger plug 60 is shown supported laterally and some axially. The stop hooks 63 are holding the plug stop 62 to further prevent the pop out plunger plug 60 from popping out under pressure. The plunger 1 is shown inside of the syringe module 2. The barrier support 54 is shown in alignment with the frangible ring 77. The barrier support 54 is shown with a slop 84 at the distal end to place a concentrated load on the frangible ring 77.

Figure 47:
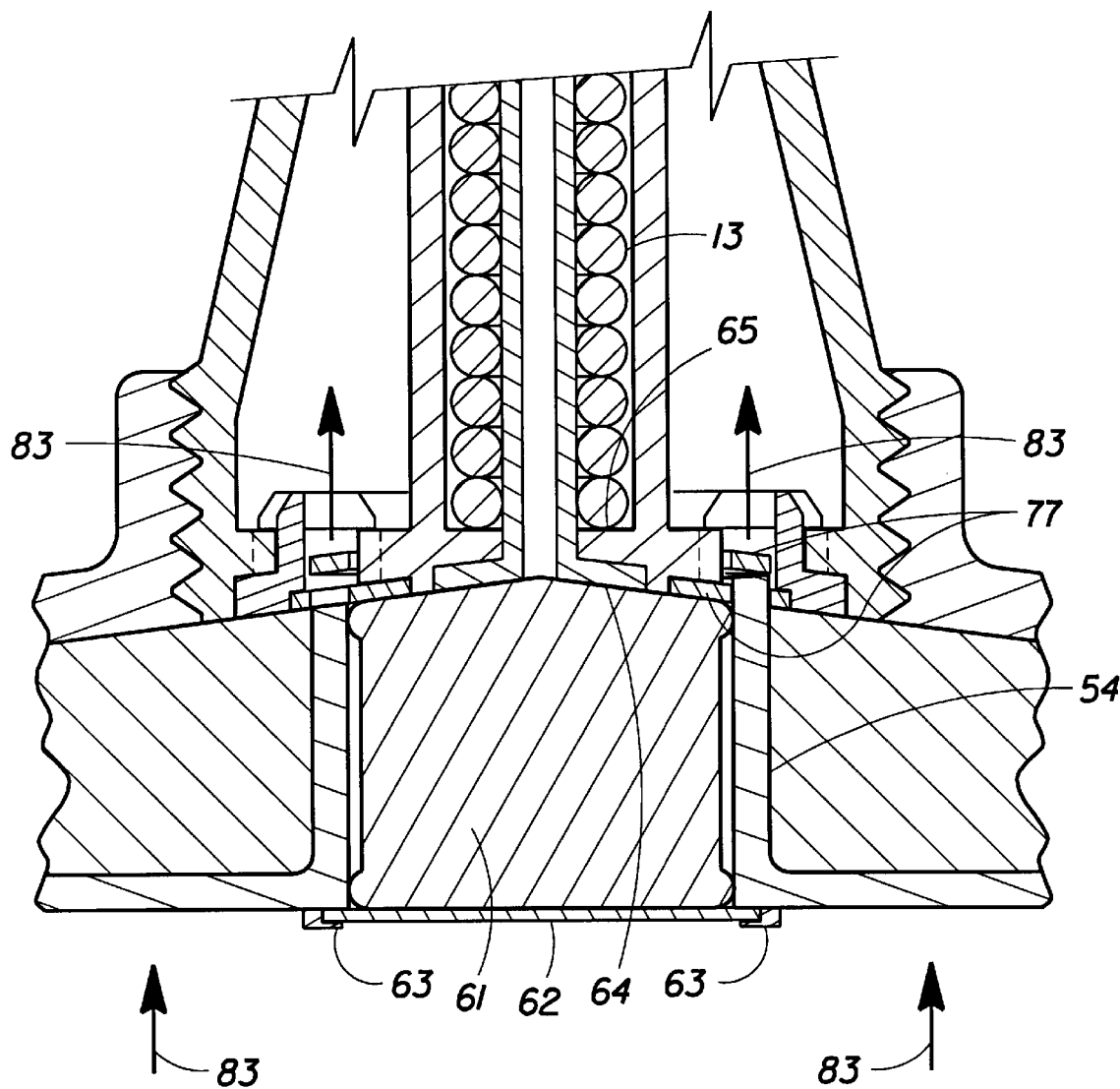
FIG. 47 is a section elevation of the plunger being thrust into the needle cannula module.

Referring to FIG. 47 there is shown an elongated section elevation of the plunger being thrust in a distal direction 38.

The distal end of the barrier support 54 has come in contact with the frangible ring 77 and exerted a concentrated load or point load on the frangible ring 77. The frangible ring 77 has broken and the frangible plate no longer restrains the thrust of the biased spring 13 and the biased spring is now thrusting on the spring foundation 65, needle cannula 8, and the cone flange 64.

As the cone flange is released it is thrust into the pop out plunger plug 61 and a load is further exerted on the pop out plunger plug, as the plunger is thrust into a distal direction 83. The pop out plunger plug is now exerting a load on the plug stop 62 and the stop hook 63.

Figure 48:
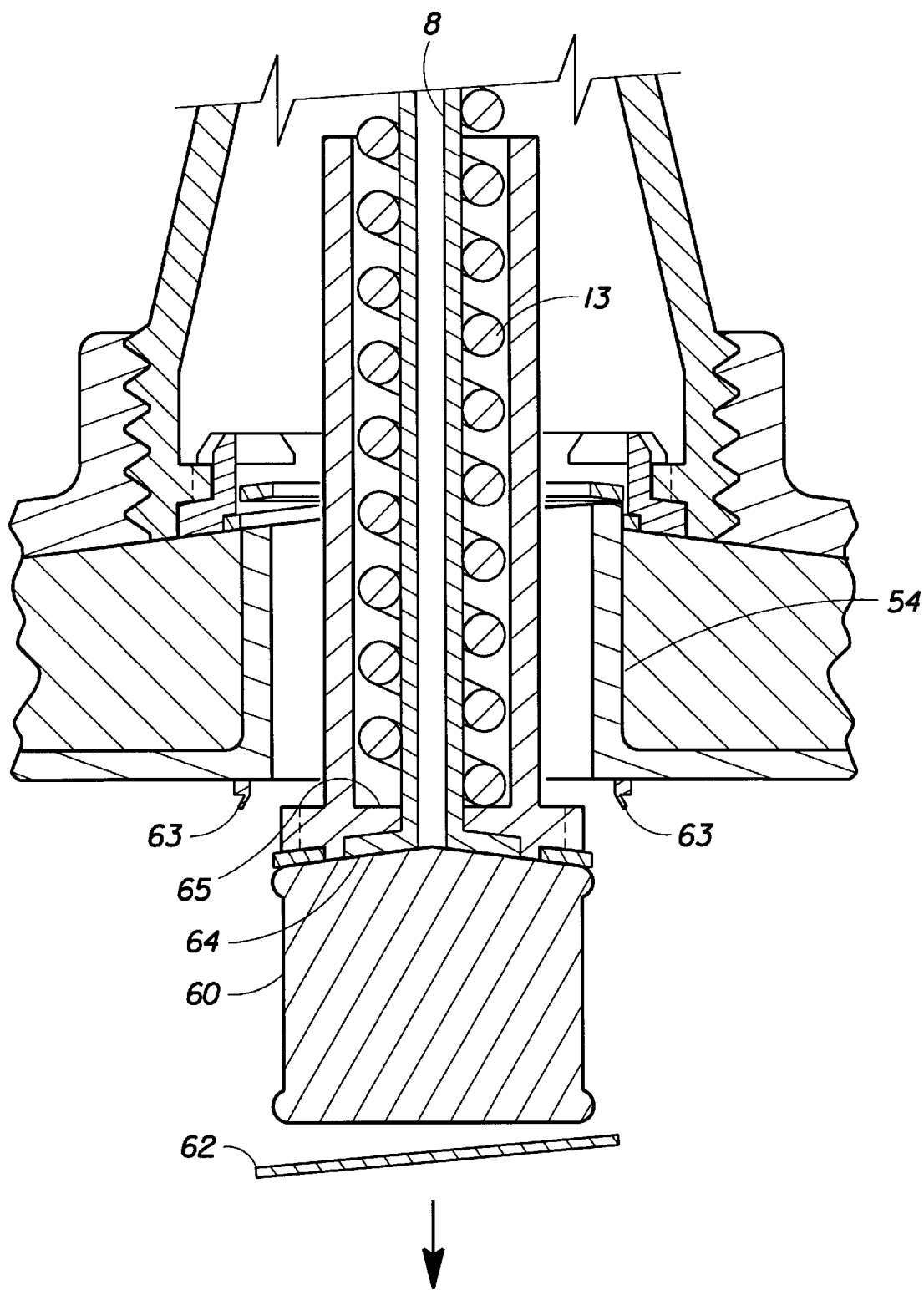
FIG. 48 is a section elevation of the device being broken apart.

Referring to FIG. 48 there is shown a section elevation of the biased spring 13 thrusting the needle cannula 8, the spring foundation 65 and the cone flange 64 into the pop out plunger plug 60 thereby causing the stop hook 63 to break and thus release the plug stop 62 and the pop out plunger plug from the barrier support 54. The biased spring continues to thrust the needle cannula into the plunger.

Figure 49:
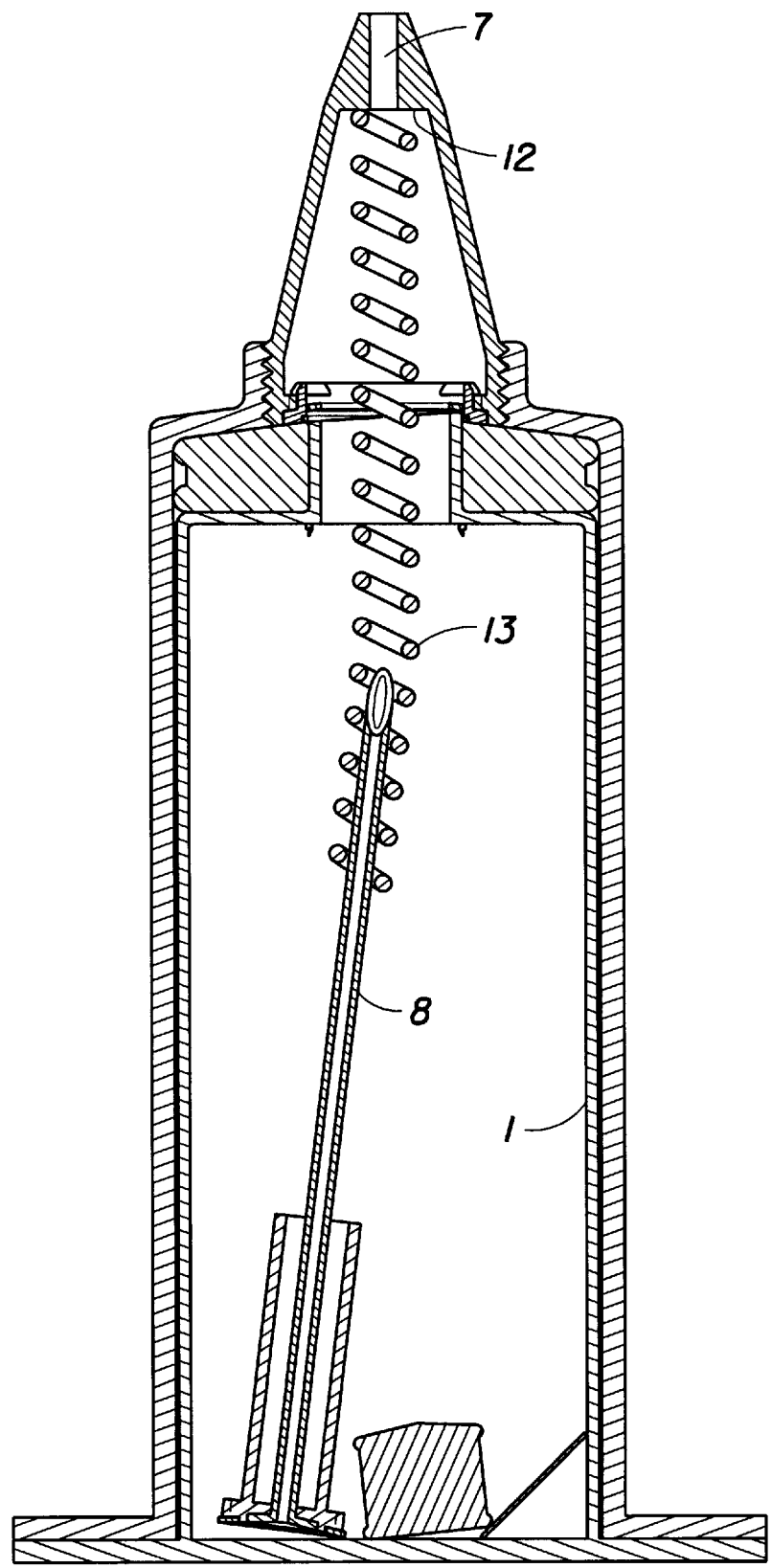
FIG. 49 is a section elevation of the needle cannula inside the plunger and syringe module.

Referring to FIG. 49 there is shown a section elevation of the needle cannula 8 inside of the plunger 1. The spring 13 will remain where it is to prevent the distal end of the needle cannula from re-entering the support tunnel 7 and thereby injuring someone. The distal end of the spring is fixed to the cannula flat 12 and thereby will not let the needle cannula out of the support tunnel.

What is claimed as invention is:

1. An interchangeable safety needle cannula module that is activated by a safety syringe module comprised of:

a safety needle cannula module with a distal end and a proximal end wherein the safety needle cannula module is hollow with an inside surface and an outside surface and wherein threads are formed on said outside surface near said proximal end and wherein a module flange is formed on said proximal end of said safety needle cannula module and wherein said module flange extends inward from said safety needle cannula module;

a needle cannula with a distal end and a proximal end wherein said distal end extends from said safety needle cannula module and a needle base plate that is formed at said proximal end of said needle cannula;

a base plate with a distal end and a proximal end and wherein a base plate flange is formed on the outer periphery of said base plate;

a retaining ring with a distal end and a proximal end and an outer periphery and an inner periphery and wherein said retaining ring extends from said base plate to said module flange;

a syringe module with a distal end and a proximal end wherein said syringe module is hollow with an inside surface and an outside surface and wherein said distal end and inside surface of said syringe module has threads formed and wherein said inside threads are equal to said outside threads formed on said proximal end of said safety needle cannula module and said safety needle cannula module screws into said syringe module;

a plunger with a distal end and a proximal end wherein said plunger is an elongated hollow tube with an inside surface and an outside surface and wherein a dome foundation is formed on said inside surface at said distal end of said plunger and wherein a dome notch is formed in said dome foundation;

a pop out dome with a distal end, a proximal end and an outer periphery wherein a dome flange is formed and wherein said dome flange is disposed in said dome notch formed in said dome foundation and wherein said distal end of said plunger is in alignment with said retaining ring and wherein said plunger is thrust into said retaining ring and wherein said distal end of said plunger thrusts said retaining ring off of said base plate flange and off of said module flange and wherein said base plate flange further causes a concentrated load on said pop out dome causing said pop out dome to deflect wherein said pop out dome will rotate about said peripherial end and said pop out dome will reverse and thereby said dome flange will pop out of said dome notch and said pop out dome will fall out of said dome foundation.

2. The syringe of claim 1 wherein said retaining ring has V notches formed on the inner periphery and the outer periphery and wherein the configuration of said inner periphery and said outer periphery of said retaining ring match the beveled configuration of the outside periphery of said base plate flange and beveled configuration of the inner periphery of said modular flange.

3. The syringe of claim 1 wherein said retaining ring is an O shape in section and wherein said modular flange and said base plate flange have a configuration to accommodate the O configuration.

4. The syringe of claim 1 wherein said retaining ring is an H retaining ring in section and wherein each leg of said H retaining ring laps over each side of the inner periphery of the modular flange and each side of the outer periphery of the base plate flange.

5. The syringe of claim 1 wherein said retaining ring is a friction ring and wherein the outer periphery of said base plate flange is fixed to the inner periphery of the friction ring and wherein the inner periphery of the module flange is fixed to the outer periphery of the friction ring by friction.

6. The syringe of claim 5 wherein adhesive fixes said outer periphery of said friction ring to said inner periphery of said module flange.

7. The syringe of claim 5 wherein adhesive fixes said inner periphery of friction ring to said outer periphery of said base plate flange.

8. The syringe of claim 1 wherein said pop out dome will withstand great hydrostatic pressure and wherein said pop out dome will turn inside out with a concentrated load.

9. The syringe of claim 1 wherein said pop out dome is further comprised of:
  a dome flange wherein said dome flange essentially extends around the outer periphery of said pop out dome;
  a dome trunnion wherein said dome trunnion is formed near the outer periphery of said pop out dome and wherein said dome trunnion extends from near said distal end of said pop out dome to said proximal end of said pop out dome;
  a dome foundation wherein said dome foundation extends inward from said dome support means and wherein a dome notch is formed in said dome foundation and said dome notch is essentially circumambient in said dome foundation and wherein said dome flange is disposed in said dome notch and when a hydrostatic load is applied to said pop out dome, said pop out dome will not change shape, however, when a concentrated load is applied to said pop out dome said pop out dome will deflect and form a reverse dome wherein said dome trunnion will rotate about the proximal end of the dome foundation further causing said dome flange to be withdrawn from said dome notch wherein said pop out dome will form into a reverse dome completely withdrawing said dome flange from said dome notch and wherein said pop out dome will fall into said plunger.

10. An interchangeable needle cannula module that is activated by a safety syringe module comprised of;
  a snap on needle cannula module with a distal end and a proximal end;
  a snap on flange formed on said snap on needle cannula module wherein said snap on flange has a distal end and a proximal end;
  an outer syringe flange with a distal end and a proximal end;
  an inner syringe flange with a distal end and a proximal end
  a snap ring with a distal end and a proximal end wherein said snap on ring is disposed about said snap on flange and wherein said distal end of said snap on flange is placed on said outer syringe flange and said proximal end of said snap on flange is disposed between said outer syringe flange and said inner syringe flange and wherein said snap ring is disposed over said snap on flange and said snap ring is rotated about said snap on flange until said snap ring locks said outer syringe flange.

11. The interchangeable needle cannula module of claim 10 wherein said interchangeable needle cannula module is further comprised of;
  a needle cannula with a distal end and a proximal end;
  a base plate with a distal end and a proximal end and a cannula formed in said base plate wherein said cannula extends from said distal end to said proximal end of said base plate and wherein said proximal end of said needle cannula is fixed to said distal end of said base plate;
  a retaining ring with a distal end and a proximal end wherein said retaining ring extends from said base plate to said snap on needle cannula module near said distal end of said snap on needle cannula module;
  a biased spring with a distal end and a proximal end wherein said biased spring is disposed about said needle cannula and said biased spring is thrusting on said proximal end of said base plate;
  a plunger wherein said plunger is an elongated hollow tube with a distal end and a proximal end;
  a plug support means with a distal end and a proximal end wherein said proximal end of said plug support means is fixed to said distal end of said plunger;
  a double flange plug with a distal end and a proximal end wherein said proximal end of said double flange plug is disposed about said plug support means;
  a compressible plunger seal with a distal end and a proximal end wherein said compressible plunger seal has compressor chambers formed in said compressible plunger seal and wherein said snap on needle cannula module is attached to said snap on syringe and wherein said snap on syringe and said snap on needle cannula module are used to inject medication into a body wherein said plunger further thrusts said distal end of said plug support means into said retaining ring wherein said retaining ring is disengaged with said proximal end of said needle cannula module and wherein said plunger further thrusts said double flange plug into said base plate further causing said double flange plug to disengage with said plunger flange further causing said double flange plug to be thrust into said plunger and thereby cause said biased spring to thrust said base plate and said needle cannula into said plunger thus containing said needle cannula in said plunger.

12. The interchangeable needle cannula module of claim 11 wherein said compressible plunger seal is compressed forcing said compressor chambers to be compressed.

13. The interchangeable needle cannula module of claim 11 wherein said retaining ring is formed into an H in section.

14. The interchangeable needle cannula module of claim 11 wherein said retaining ring is a friction ring.

15. An interchangeable needle cannula module that is activated by a plunger comprised of;
   a safety needle cannula module with a distal end and a proximal end wherein said safety needle cannula module is essentially hollow with an inside surface and an outside surface and wherein an attachment means is formed on the outside surface near the proximal end of said safety needle cannula module;
   a spring shield with a distal end and a proximal end wherein said spring shield is an elongated hollow tube with an outside surface and with a base plate and a base plate flange formed near said proximal end of said spring shield;
   a biased spring with a distal end and a proximal end wherein said proximal end of said biased spring is thrusting on said base plate and said biased spring is disposed in said spring shield;
   a needle cannula with a distal end and a proximal end wherein said distal end of said needle cannula extends past said distal end of said safety needle cannula module and said proximal end of said needle cannula is fixed to said base plate of said spring shield and said needle cannula is disposed in said biased spring;
   a ring with a distal end and a proximal end, an inner periphery and an outer periphery and wherein said ring is held between said inside surface of said syringe module and said outside surface of said base plate flange;
   a syringe module formed into an elongated hollow tube with a distal end and a proximal end, with an inside surface and an outside surface and with an attachment means formed on said distal end of said syringe module wherein said attachment means at said proximal end of said safety needle cannula module will attach to said attachment means at said proximal end of said syringe module;
   a plunger module with a distal end and a proximal end wherein said plunger module is an elongated hollow cylinder with an inside surface and an outside surface and wherein a barrier support is formed on said distal end of said plunger module wherein said barrier support has a distal end and a proximal end and wherein said distal end of said barrier support is essentially the same diameter of said ring;
   a plunger barrier with a distal end and a proximal end and an outer periphery wherein said plunger barrier is supported on said distal end of said barrier support and wherein said plunger is thrust into a distal direction thereby thrusting said distal end of said barrier support into said ring thereby disengaging said ring from said base plate flange and said module flange and further thrusting said plunger barrier into said base plate and said base plate flange, further causing said base plate to thrust against said plunger barrier thereby forcing said plunger barrier into said plunger and further allowing said biased spring to thrust said spring shield and said needle cannula into said plunger thereby rendering said needle cannula harmless.

16. The interchangeable needle cannula module of claim 15 wherein said ring is held by the module flange and the base plate flange is held by friction only.

17. The interchangeable needle cannula module of claim 15 wherein said ring is held by the module flange and the base plate flange is held by adhesive.

18. The interchangeable needle cannula module of claim 15 wherein said ring is held by the module flange and the base plate flange by other bonding means.

19. The interchangeable needle cannula module of claim 15 wherein a barrier foundation is formed at the distal end of said barrier support and wherein a barrier notch is formed in said barrier foundation and wherein a barrier flange is formed on said outer periphery of said plunger barrier and said barrier flange is disposed in said barrier notch and wherein when said plunger barrier is thrust into said base plate and said base plate flange, said barrier flange will fail to hold said plunger barrier and will further disengage from said barrier notch.

20. A interchangeable safety needle cannula module that is activated by a safety syringe module and a plunger comprised of:
   a safety needle cannula module with a distal end and a proximal end wherein said safety needle cannula module is essentially hollow with an inside surface and an outside surface and wherein an attachment means is formed on the outside surface near the proximal end of said safety needle cannula module
   a syringe module with a distal end and a proximal end wherein said syringe module is an elongated hollow tube with an inside surface and an outside surface and wherein an attachment means is formed on said distal end of said syringe module wherein said safety needle cannula module may be attached to said syringe module;
   a needle cannula with a distal end and a proximal end and wherein said distal end of said needle cannula extends past said distal end of said needle cannula module wherein a cone flange is formed at said proximal end of said needle cannula wherein said cone flange has a distal end and a proximal end;
   a module flange formed on the inside surface near said proximal end of said safety needle cannula module wherein said module flange has and inside periphery with at least one notch formed on said inside periphery of said module flange;
   a tab support ring with an inside periphery an outside periphery a distal end and a proximal end and wherein a ring flange is formed on said proximal end of said tab support ring and wherein said ring flange extends around the outside periphery of said tab support ring and at least one outer tab is formed on said distal end and said outer periphery of said tab support ring and at least one inner tab is formed on said inside periphery near said distal end of said tab support ring;
   a frangible ring with a distal end and a proximal end, an inside periphery end an outer periphery wherein said frangible ring is fixed to said inside periphery at said proximal end of said tab support ring;
   a support flange with a distal end and a proximal end and with an outer periphery wherein at least one support flange slot is formed in said outer periphery of said support flange and wherein said support flange is fixed to said spring foundation;
   a biased spring with a distal end and a proximal end wherein said distal end of said biased spring is thrusting on said distal end of said safety needle cannula module and wherein said proximal end of said biased spring is thrusting on said spring foundation and wherein said biased spring is disposed about said needle cannula;
   a plunger with a distal end and a proximal end wherein said plunger is an elongated hollow cylinder with an inside surface and an outside surface and wherein a barrier support is formed near said distal end of said plunger and wherein said barrier support is an elongated hollow cylinder that is essentially the same diameter as said frangible plate wherein said plunger is thrust in a distal direction thereby thrusting said barrier support in a distal direction wherein said barrier support engages said frangible ring wherein said barrier support causes said frangible ring exerting a concentrated load on said frangible ring wherein said frangible ring will break thereby releasing said cone flange, said support flange, said spring foundation and said needle cannula wherein said biased spring will thrust said needle cannula into said plunger.

* * * * *